United States Patent [19]

Yamashita et al.

[11] Patent Number: 5,719,145
[45] Date of Patent: Feb. 17, 1998

[54] AMIDINE DERIVATIVES AND PLATELET AGGREGATION INHIBITOR CONTAINING THE SAME

[75] Inventors: Hiroyuki Yamashita; Kunio Okumura; Toshiyuki Shimazaki, all of Chiba-ken; Akihito Kanematsu, Aichi-ken; Yoji Aoki, Chiba-ken; Yuki Nakajima, Chiba-ken; Kouhei Yazawa, Chiba-ken; Kenji Kibayashi, Chiba-ken, all of Japan

[73] Assignee: Mitsui Toatsu Chemicals, Inc., Tokyo, Japan

[21] Appl. No.: 699,346

[22] Filed: Aug. 19, 1996

[51] Int. Cl.$^6$ .................. A61K 31/54; A61K 31/535; C07D 311/04; C07D 311/76
[52] U.S. Cl. .................. 514/226.8; 514/228.2; 514/233.5; 514/444; 514/457; 514/337; 514/256; 514/253; 514/320; 544/151; 544/62; 546/282.7; 549/60; 549/404; 549/405
[58] Field of Search .................. 549/404, 405, 549/60; 546/282.7; 544/151, 62; 514/233.5, 444, 457, 337, 228.2, 226.8, 256, 253, 320

[56] References Cited

FOREIGN PATENT DOCUMENTS

| | | |
|---|---|---|
| 0635492 | 1/1995 | European Pat. Off. . |
| 0709370 | 5/1996 | European Pat. Off. . |
| WO94/29273 | 12/1994 | WIPO . |
| WO 9622288 | 7/1996 | WIPO . |

OTHER PUBLICATIONS

Cook et al, "Platelet Glycoprotein IIB/IIIa Antagonists", *Drugs of the Future*, 19(2), pp. 135–159, 1994.

Weller et al, "Fibrinogen Receptor Antagonists—A Novel Class of Promising Antithrombotics", *Drugs of the Future*, 19(5), pp. 461–476, 1994.

D. Huckle et al, "3–Amino–4–Chromanone Hydrochlorides", *J. Med. Chem.*, 12, pp. 277–279, 1969.

*Primary Examiner*—Mukund J. Shah
*Assistant Examiner*—Bruce Kifle
*Attorney, Agent, or Firm*—Burns, Doane, Swecker & Mathis

[57] ABSTRACT

The invention relates to a substituted amidine derivative which has an excellent platelet aggregation inhibiting action on the basis of fibrinogen antagonism and is particularly excellent in effectiveness on oral administration, and the platelet aggregation inhibitor containing the substituted amidine derivative of the invention as an effective ingredient is effective for prevention and treatment of thrombosis, and restenosis or reocclusion after percutaneous transluminal coronary angioplasty or percutaneous transluminal coronary recanalization.

20 Claims, No Drawings

AMIDINE DERIVATIVES AND PLATELET AGGREGATION INHIBITOR CONTAINING THE SAME

BACKGROUND OF THE INVENTION

1) Field of the Invention

The present invention relates to a novel substituted amidine derivative which inhibits binding of a platelet fibrinogen receptor GP IIb/IIIa to fibrinogen and a platelet aggregation inhibitor containing the said derivative.

2) Description of Related Art

Various medicines for inhibiting aggregation of platelets have been used for curing thrombosis since platelets were found to play an important role for thrombosis. Aggregation of platelets is induced by various stimuli such as ADP, collagen, epinephrine, thrombin, thromboxane $A_2$ and platelet activating factors. Therefore, anti-platelet drugs exhibit an inhibiting effect merely against platelet aggregation caused by restricted kinds of stimuli and thus efficacy of these drugs is limited.

The final step in the platelet aggregation process is mutual binding of platelets by way of fibrinogen. The step is common and independent upon the kind of aggregation eliciting stimulus. Consequently, in recent years, a drug which directly inhibits binding of platelets and fibrinogen (fibrinogen antagonist) has received attention as an antiplatelet drug having an inhibitory function for the whole aggregation eliciting stimuli. It has been found that the binding site of fibrinogen for platelets is glycoprotein GP IIb/IIIa which is present in a platelet membrane and that the structure of -Arg-Gly-Asp- in a fibrinogen molecule is a minimum amino acid sequence which is required for binding with GP IIb/IIIa. Many non-peptide compounds which are similar in structure to the straight chain or cyclic peptide compound having the amino acid sequence of -Arg-Gly-Asp- have been reported thereafter [Drug of the Future, 19(2), 135 (1994) and 19(5), 461 (1994)]. The common structure of the so far known non-peptide compounds has an acid group such as a carboxyl group which corresponds to a carboxyl group in aspartic acid and additionally has in a certain distance a basic group such as an amidino group, guanidino group, piperidyl group and aminomethyl group which correspond to a guanidino group in arginine. Further, diversity has been found on the skeleton structure which connects the acid group with the basic group. Compounds having a bicyclic structure formed by condensation of two six-membered rings as the skeleton structure has been disclosed in WO94/29273 and EP-A 0635492. However, compounds disclosed in WO94/29273 has inhibiting action of 1–13 μM for human platelet aggregation and thus activity is unsatisfactory. As to basic groups, WO94/29273 has described an amidino group, alkylamidino group and alkoxycarbonylamidino group, and EP-A 0635492 has also described an amidino group. However, these compounds have been found to have insufficient effectiveness on oral administration.

One object of the invention is to provide a compound having a strong platelet aggregation inhibiting action and excellent effectiveness on oral administration.

Another object of the invention is to provide a preventive or a remedy for thrombosis such as an ischemic heart disease, ischemic brain disease, peripheral circulatory impairment, arterial thrombus, arterial sclerosis and angiopulmonary impairment, and also for restenosis and reocclusion after percutaneous transluminal coronary angioplasty or percutaneous transluminal coronary recanalization.

SUMMARY OF THE INVENTION

As a result of an intensive investigation on a non-peptide compound having a fibrinogen antagonism, the present inventors have found that a compound having an amidino group modified with a specific substituent has a strong platelet aggregation inhibiting action as a fibrinogen antagonist and excellent effectiveness on oral administration and additionally has extremely increased solubility in water and various solvents. Thus the present invention has been completed.

That is, one aspect of the invention is a substituted amidine derivative represented by formula (1):

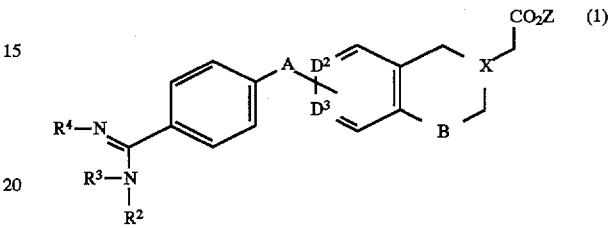

wherein A is —CON($R^1$)— or —N($R^1$)CO— and is bonded to $D^2$ or $D^3$, wherein $R^1$ is a hydrogen atom or an alkyl group having 1–4 carbon atoms, and $D^2$ and $D^3$ is a carbon atom; B is —$CH_2$— or —O—, and X is

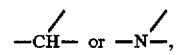

and X excludes

when B is —O—; Z is a hydrogen atom, an unsubstituted or substituted alkyl group; $R^2$, $R^3$ and $R^4$ are a hydrogen atom, alkyl group having 1–4 carbon atoms, propargyl group, $R^5O(CO)$— or —$(CH_2)_m$— Het, wherein $R^5$ is an alkyl group having 1–4 carbon atoms or 2-methyoxyethyl group, m is an integer of 1 or 2, Het is a heterocyclic group containing a hetero atom such as a nitrogen, oxygen and sulfur atom, or $R^2$ and $R^3$ are bonded to form —$(CH_2)_n$—W—$(CH_2)_p$—, wherein n and p are an integer of 2 or 3, a certain position on the methylene chain is unsubstituted or substituted with an alkyl group having 1–4 carbon atoms or an alkoxy group having 1–4 carbon atoms, W is a direct bond, —$CH_2$—, —O—, —N($R^6$)— or —$S(O)_q$—, wherein $R^6$ is an alkyl group having 1–4 carbon atoms, phenyl group or pyridyl group and q is 0 or an integer of 1 or 2; one or more groups in $R^2$, $R^3$ and $R^4$ are selected from the group wherein a hydrogen atom, alkyl group having 1–4 carbon atoms and $R^5O(CO)$— are exclusive; or a pharmaceutically acceptable salt thereof.

Another aspect of the invention is a platelet aggregation inhibitor comprising a substituted amidine derivative represented by formula (1) as an effective ingredient.

A further aspect of the invention is a method for preventing or treating thrombosis, comprising administering an effective amount of a substituted amidine derivative represented by formula (1).

A still further aspect of the invention is a method for preventing or treating restenosis after percutaneous transluminal coronary angioplasty or percuteneous transluminal coronary recanalization, comprising administering an effective amount of a substituted amidine derivative represented by formula (1).

A still further aspect of the invention is a method for preventing or treating reocclusion after percutaneous transluminal coronary angioplasty or percutaneous transluminal coronary recanalization, comprising administering an effective amount of a substituted amidine derivative represented by formula (1).

DETAILED DESCRIPTION OF THE INVENTION

The present invention will be illustrated in detail hereinafter.

The active form of the substituted amidine derivative represented by formula (1) in the invention is a carboxylic acid type compound wherein Z is a hydrogen atom. Further, the so-called prodrug which can convert to the carboxylic acid type active form in a human body is also similarly effective. Various kinds of such prodrug have been conventionally known. In the case of the invention, an ester-type prodrug wherein Z is an unsubstituted or substituted alkyl group is particularly effective.

The unsubstituted and substituted alkyl groups represented by Z include, for example, a methyl, ethyl, n-propyl, isopropyl, isobutyl, sec-butyl, tert-butyl, n-butyl, n-pentyl, isopentyl, neopentyl, tert-pentyl, n-hexyl, isohexyl, n-heptyl, isoheptyl, n-octyl, isooctyl group and other alkyl groups having 1–8 carbon atoms; 2-hydroxyethyl group; 2-methoxyethyl group; aralkyl groups such as a benzyl, phenetyl, 1-phenylethyl, 3-phenylpropyl, 2-phenylpropyl, 1-phenylpropyl, 1-methyl-2-phenylethyl, 4-phenylbutyl, 3-phenylbutyl, 2-phenylbutyl, 1-phenylbutyl, 2-methyl-3-phenylpropyl, 2-methyl-2-phenylpropyl, 5-phenylpentyl, 6-phenylhexyl and 2-naphthylmethyl group; acyloxyalkyl groups such as an acetoxymethyl, 1-acetoxyethyl, pivaloyloxymethyl, 2,2-dimethylpropanoyloxymethyl, 1-(pivaloyloxy)ethyl and 1-(pivaloyloxy)propyl group; and alkoxycarbonyloxyalkyl groups such as a methoxycarbonyloxymethyl, 1-(methoxycarbonyloxy)ethyl, 2-methoxycarbonyloxy)ethyl and ethoxycarbonyloxymethyl group. Preferred groups are alkyl groups having 1–8 carbon atoms, 2-hydroxyethyl group or 2-methoxyethyl group.

$R^1$ is a hydrogen atom or an alkyl group having 1–4 carbon atoms which includes, for example, a methyl, ethyl, n-propyl, isopropyl, isobutyl, sec-butyl, tert-butyl and n-butyl group. The hydrogen atom is preferred.

$R^2$, $R^3$ and $R^4$ are a hydrogen atom, alkyl group having 1–4 carbon atoms which includes, for example, a methyl, ethyl, n-propyl, isopropyl, isobutyl, sec-butyl, tert-butyl and n-butyl group; $R^5O(CO)$— wherein $R^5$ is an alkyl group having 1–4 carbon atoms which includes, for example, a methyl, ethyl, n-propyl, isopropyl, isobutyl, sec-butyl, tertbutyl and n-butyl group and 2-methoxyethyl group; —$(CH_2)_m$-Het wherein m is an integer of 1 or 2, Het is a heterocyclic group containing a heteroatom such as a nitrogen, oxygen and sulfur atom, for example, a 2-furyl, 3-furyl, 2-thienyl, 3-thienyl, 2-pyridyl, 3-pyridyl and 4-pyridyl group wherein the 2-furyl group is preferred; and a propargyl group.

The group —$(CH_2)_n$—W—$(CH_2)_p$— is formed by bonding $R^2$ with $R^3$ and is unsubstituted or substituted at a certain position on the methylene chain with an alkyl group having 1–4 carbon atoms which includes, for example, a methyl, ethyl, n-propyl, isopropyl, isobutyl, sec-butyl, tert-butyl and n-butyl group or with an alkoxy group having 1–4 carbon atoms which includes, for example, a methoxy, ethoxy, n-propoxy, isopropoxy, isobutoxy, sec-butoxy, tert-butoxy and n-butoxy group. When the group —$(CH_2)_n$—W—$(CH_2)_p$— is illustrated by the name of cyclic amino group which contains a nitrogen atom bonded with $R^2$ and $R^3$, exemplary cyclic amino groups include, for example, a pyrrolidinyl, piperidyl, homopiperidyl, piperazinyl, homopiperazinyl, 4-methylpiperazinyl, 4-ethylpiperazinyl, 4-phenylpiperazinyl, 4-(2-pyridyl)piperazinyl, 4-(3-pyridyl) piperazinyl, 4-(4-pyridyl)piperazinyl, 4-methoxypiperidyl, 4-ethoxypiperidyl, 4-n-butoxypiperidyl, morpholinyl, homomorpholinyl, thiomorpholinyl and homothiaomorpholinyl group.

However, one or more of $R^2$, $R^3$ and $R^4$ are selected from the group wherein a hydrogen atom, alkyl group having 1–4 carbon atoms and $R^5O(CO)$— are exclusive. A preferred form is a cyclic structure of —$(CH_2)_n$—W—$(CH_2)_p$— which is formed by bonding $R^2$ with $R^3$.

Representative compounds having formula (1) of the invention will be specifically exemplified hereinafter. However, these enumerated compounds are not construed to limit the scope of the invention.

(1) 7-[[4-(morpholinoiminomethyl)benzoyl]amino]-1,2,3,4-tetrahydronaphthalene-2-acetic acid (2) methyl 7-[[4-(morpholinoiminomethyl)benzoyl]amino]-1,2,3,4-tetrahydronaphthalene-2-acetate (3) ethyl 7-[[4-(morpholinoiminomethyl)benzoyl]amino]-1,2,3,4-tetrahydronaphthalene-2-acetate (4) 2-hydroxyethyl 7-[[4-(morpholinoiminomethyl)benzoyl]amino]-1,2,3,4-tetrahydronaphthalene-2-acetate (5) 2-methoxyethyl 7-[[4-(morpholinoiminomethyl)benzoyl]amino]-1,2,3,4-tetrahydronaphthalene-2-acetate (6) n-propyl 7-[[4-(morpholinoiminomethyl)benzoyl]amino]-1,2,3,4-tetrahydronaphthalene-2-acetate (7) n-butyl 7-[[4-(morpholinoiminomethyl)benzoyl]amino]-1,2,3,4-tetrahydronaphthalene-2-acetate (8) tert-butyl 7-[[4-(morpholinoiminomethyl)benzoyl]amino]-1,2,3,4-tetrahydronaphthalene-2-acetate (9) n-pentyl 7-[[4-(morpholinoiminomethyl)benzoyl]amino]-1,2,3,4-tetrahydronaphthalene-2-acetate

(10) n-hexyl 7-[[4-(morpholinoiminomethyl)benzoyl]amino]-1,2,3,4-tetrahydronaphthalene-2-acetate

(11) n-heptyl 7-[[4-(morpholinoiminomethyl)benzoyl]amino]-1,2,3,4-tetrahydronaphthalene-2-acetate

(12) n-octyl 7-[[4-(morpholinoiminomethyl)benzoyl]amino]-1,2,3,4-tetrahydronaphthalene-2-acetate

(13) 6-[[4-(morpholinoiminomethyl)benzoyl]amino]-1,2,3,4-tetrahydronaphthalene-2-acetic acid

(14) methyl 6-[[4-(morpholinoiminomethyl)benzoyl]amino]-1,2,3,4-tetrahydronaphthalene-2-acetate

(15) ethyl 6-[[4-(morpholinoiminomethyl)benzoyl]amino]-1,2,3,4-tetrahydronaphthalene-2-acetate

(16) 2-hydroxyethyl 6-[[4-(morpholinoiminomethyl)benzoyl]amino]-1,2,3,4-tetrahydronaphthalene-2-acetate

(17) 2-methoxyethyl 6-[[4-(morpholinoiminomethyl)benzoyl]amino]-1,2,3,4-tetrahydronaphthalene-2-acetate

(18) n-propyl 6-[[4-(morpholinoiminomethyl)benzoyl]amino]-1,2,3,4-tetrahydronaphthalene-2-acetate

(19) n-butyl 6-[[4-(morpholinoiminomethyl)benzoyl]amino]-1,2,3,4-tetrahydronaphthalene-2-acetate

(20) n-heptyl 6-[[4-(morpholinoiminomethyl)benzoyl]amino]-1,2,3,4-tetrahydronaphthalene-2-acetate

(21) n-octyl 6-[[4-(morpholinoiminomethyl)benzoyl]amino]-1,2,3,4-tetrahydronaphthalene-2-acetate

(22) 6-[[4-(morpholinoiminomethyl)benzoyl]amino] chroman-3-acetic acid

(23) methyl 6-[[4-(morpholinoiminomethyl)benzoyl]amino] chroman-3-acetate

(24) ethyl 6-[[4-(morpholinoiminomethyl)benzoyl]amino]chroman-3-acetate
(25) 2-hydroxyethyl 6-[[4-(morpholinoiminomethyl)benzoyl]amino]chroman-3-acetate
(26) 2-methoxyethyl 6-[[4-(morpholinoiminomethyl)benzoyl]amino]chroman-3-acetate
(27) n-propyl 6-[[4-(morpholinoiminomethyl)benzoyl]amino]chroman-3-acetate
(28) n-butyl 6-[[4-(morpholinoiminomethyl)benzoyl]amino]chroman-3-acetate
(29) n-heptyl 6-[[4-(morpholinoiminomethyl)benzoyl]amino]chroman-3-acetate
(30) n-octyl 6-[[4-(morpholinoiminomethyl)benzoyl]amino]chroman-3-acetate
(31) 7-[[4-(morpholinoiminomethyl)benzoyl]amino]chroman-3-acetic acid
(32) methyl 7-[[4-(morpholinoiminomethyl)benzoyl]amino]chroman-3-acetate
(33) ethyl 7-[[4-(morpholinoiminomethyl)benzoyl]amino]chroman-3-acetate
(34) 2-hydroxyethyl 7-[[4-(morpholinoiminomethyl)benzoyl]amino]chroman-3-acetate
(35) 2-methoxyethyl 7-[[4-(morpholinoiminomethyl)benzoyl]amino]chroman-3-acetate
(36) n-propyl 7-[[4-(morpholinoiminomethyl)benzoyl]amino]chroman-3-acetate
(37) n-butyl 7-[[4-(morpholinoiminomethyl)benzoyl]amino]chroman-3-acetate
(38) n-heptyl 7-[[4-(morpholinoiminomethyl)benzoyl]amino]chroman-3-acetate
(39) n-octyl 7-[[4-(morpholinoiminomethyl)benzoyl]amino]chroman-3-acetate
(40) 7-[[4-(morpholinoiminomethyl)benzoyl]amino]-1,2,3,4-tetrahydroisoquinoline-2-acetic acid
(41) methyl 7-[[4-(morpholinoiminomethyl)benzoyl]amino]-1,2,3,4-tetrahydroisoquinoline-2-acetate
(42) ethyl 7-[[4-(morpholinoiminomethyl)benzoyl]amino]-1,2,3,4-tetrahydroisoquinoline-2-acetate
(43) n-propyl 7-[[4-(morpholinoiminomethyl)benzoyl]amino]-1,2,3,4-tetrahydroisoquinoline-2-acetate
(44) n-butyl 7-[[4-(morpholinoiminomethyl)benzoyl]amino]-1,2,3,4-tetrahydroisoquinoline-2-acetate
(45) 2-hydroxyethyl 7-[[4-(morpholinoiminomethyl)benzoyl]amino]-1,2,3,4-tetrahydroisoquinoline-2-acetate
(46) 2-methoxyethyl 7-[[4-(morpholinoiminomethyl)benzoyl]amino]-1,2,3,4-tetrahydroisoquinoline-2-acetate
(47) n-octyl 7-[[4-(morpholinoiminomethyl)benzoyl]amino]-1,2,3,4-tetrahydroisoquinoline-2-acetate
(48) 6-[[4-(morpholinoiminomethyl)benzoyl]amino]-1,2,3,4-tetrahydroisoquinoline-2-acetic acid
(49) methyl 6-[[4-(morpholinoiminomethyl)benzoyl]amino]-1,2,3,4-tetrahydroisoquinoline-2-acetate
(50) ethyl 6-[[4-(morpholinoiminomethyl)benzoyl]amino]-1,2,3,4-tetrahydroisoquinoline-2-acetate
(51) n-butyl 6-[[4-(morpholinoiminomethyl)benzoyl]amino]-1,2,3,4-tetrahydroisoquinoline-2-acetate
(52) 2-hydroxyethyl 6-[[4-(morpholinoiminomethyl)benzoyl]amino]-1,2,3,4-tetrahydroisoquinoline-2-acetate
(53) 2-methoxyethyl 6-[[4-(morpholinoiminomethyl)benzoyl]amino]-1,2,3,4-tetrahydroisoquinoline-2-acetate
(54) n-octyl 6-[[4-(morpholinoiminomethyl)benzoyl]amino]-1,2,3,4-tetrahydroisoquinoline-2-acetate
(55) 7-[N-[4-(morpholinoiminomethyl)phenyl]carbamoyl]-1,2,3,4-tetrahydronaphthalene-2-acetic acid
(56) ethyl 7-[N-[4-(morpholinoiminomethyl)phenyl]carbamoyl]-1,2,3,4-tetrahydronaphthalene-2-acetate
(57) n-butyl 7-[N-[4-(morpholinoiminomethyl)phenyl]carbamoyl]-1,2,3,4-tetrahydronaphthalene-2-acetate
(58) n-octyl 7-[N-[4-(morpholinoiminomethyl)phenyl]carbamoyl]-1,2,3,4-tetrahydronaphthalene-2-acetate
(59) 6-[N-[4-(morpholinoiminomethyl)phenyl]carbamoyl]-1,2,3,4-tetrahydronaphthalene-2-acetic acid
(60) ethyl 6-[N-[4-(morpholinoiminomethyl)phenyl]carbamoyl]-1,2,3,4-tetrahydronaphthalene-2-acetate
(61) n-butyl 6-[N-[4-(morpholinoiminomethyl)phenyl]carbamoyl]-1,2,3,4-tetrahydronaphthalene-2-acetate
(62) n-octyl 6-[N-[4-(morpholinoiminomethyl)phenyl]carbamoyl]-1,2,3,4-tetrahydronaphthalene-2-acetate
(63) 6-[N-[4-(morpholinoiminomethyl)phenyl]carbamoyl]chroman-3-acetic acid
(64) ethyl 6-[N-[4-(morpholinoiminomethyl)phenyl]carbamoyl]chroman-3-acetate
(65) n-butyl 6-[N-[4-(morpholinoiminomethyl)phenyl]carbamoyl]chroman-3-acetate
(66) n-octyl 6-[N-[4-(morpholinoiminomethyl)phenyl]carbamoyl]chroman-3-acetate
(67) 7-[N-[4-(morpholinoiminomethyl)phenyl]carbamoyl]chroman-3-acetic acid
(68) ethyl 7-[N-[4-(morpholinoiminomethyl)phenyl]carbamoyl]chroman-3-acetate
(69) n-butyl 7-[N-[4-(morpholinoiminomethyl)phenyl]carbamoyl]chroman-3-acetate
(70) n-octyl 7-[N-[4-(morpholinoiminomethyl)phenyl]carbamoyl]chroman-3-acetate
(71) 7-[N-[4-(morpholinoiminomethyl)phenyl]carbamoyl]-1,2,3,4-tetrahydroisoquinoline-2-acetic acid
(72) ethyl 7-[N-[4-(morpholinoiminomethyl)phenyl]carbamoyl]-1,2,3,4-tetrahydroisoquinoline-2-acetate
(73) n-butyl 7-[N-[4-(morpholinoiminomethyl)phenyl]carbamoyl]-1,2,3,4-tetrahydroisoquinoline-2-acetate
(74) n-octyl 7-[N-[4-(morpholinoiminomethyl)phenyl]carbamoyl]-1,2,3,4-tetrahydroisoquinoline-2-acetate
(75) 6-[N-[4-(morpholinoiminomethyl)phenyl]carbamoyl]-1,2,3,4-tetrahydroisoquinoline-2-acetic acid
(76) ethyl 6-[N-[4-(morpholinoiminomethyl)phenyl]carbamoyl]-1,2,3,4-tetrahydroisoquinoline-2-acetate
(77) n-butyl 6-[N-[4-(morpholinoiminomethyl)phenyl]carbamoyl]-1,2,3,4-tetrahydroisoquinoline-2-acetate
(78) n-octyl 6-[N-[4-(morpholinoiminomethyl)phenyl]carbamoyl]-1,2,3,4-tetrahydroisoquinoline-2-acetate
(79) 7-[[4-(thiomorpholinoiminomethyl)benzoyl]amino]-1,2,3,4-tetrahydronaphthalene-2-acetic acid
(80) methyl 7-[[4-(thiomorpholinoiminomethyl)benzoyl]amino]-1,2,3,4-tetrahydronaphthalene-2-acetate
(81) ethyl 7-[[4-(thiomorpholinoiminomethyl)benzoyl]amino]-1,2,3,4-tetrahydronaphthalene-2-acetate
(82) 2-hydroxyethyl 7-[[4-(thiomorpholinoiminomethyl)benzoyl]amino]-1,2,3,4-tetrahydronaphthalene-2-acetate
(83) 2-methoxyethyl 7-[[4-(thiomorpholinoiminomethyl)benzoyl]amino]-1,2,3,4-tetrahydronaphthalene-2-acetate
(84) n-butyl 7-[[4-(thiomorpholinoiminomethyl)benzoyl]amino]-1,2,3,4-tetrahydronaphthalene-2-acetate
(85) n-octyl 7-[[4-(thiomorpholinoiminomethyl)benzoyl]amino]-1,2,3,4-tetrahydronaphthalene-2-acetate
(86) 6-[[4-(thiomorpholinoiminomethyl)benzoyl]amino]-1,2,3,4-tetrahydronaphthalene-2-acetic acid
(87) ethyl 6-[[4-(thiomorpholinoiminomethyl)benzoyl]amino]-1,2,3,4-tetrahydronaphthalene-2-acetate
(88) n-propyl 6-[[4-(thiomorpholinoiminomethyl)benzoyl]amino]-1,2,3,4-tetrahydronaphthalene-2-acetate
(89) 2-hydroxyethyl 6-[[4-(thiomorpholinoiminomethyl)benzoyl]amino]-1,2,3,4-tetrahydronaphthalene-2-acetate
(90) 2-methoxyethyl 6-[[4-(thiomorpholinoiminomethyl)benzoyl]amino]-1,2,3,4-tetrahydronaphthalene-2-acetate
(91) n-butyl 6-[[4-(thiomorpholinoiminomethyl)benzoyl]amino]-1,2,3,4-tetrahydronaphthalene-2-acetate

(92) 6-[[4-(thiomorpholinoiminomethyl)benzoyl]amino]chroman-3-acetic acid
(93) methyl 6-[[4-(thiomorpholinoiminomethyl)benzoyl]amino]chroman-3-acetate
(94) ethyl 6-[[4-(thiomorpholinoiminomethyl)benzoyl]amino]chroman-3-acetate
(95) 2-hydroxyethyl 6-[[4-(thiomorpholinoiminomethyl)benzoyl]amino]-chroman-3-acetate
(96) 2-methoxyethyl 6-[[4-(thiomorpholinoiminomethyl)benzoyl]amino]-chroman-3-acetate
(97) n-butyl 6-[[4-(thiomorpholinoiminomethyl)benzoyl]amino]chroman-3-acetate
(98) n-octyl 6-[[4-(thiomorpholinoiminomethyl)benzoyl]amino]chroman-3-acetate
(99) 7-[[4-(thiomorpholinoiminomethyl)benzoyl]amino]chroman-3-acetic acid
(100) methyl 7-[[4-(thiomorpholinoiminomethyl)benzoyl]amino]chroman-3-acetate
(101) ethyl 7-[[4-(thiomorpholinoiminomethyl)benzoyl]amino]chroman-3-acetate
(102) 2-hydroxyethyl 7-[[4-(thiomorpholinoiminomethyl)benzoyl]amino]-chroman-3-acetate
(103) 2-methoxyethyl 7-[[4-(thiomorpholinoiminomethyl)benzoyl]amino]-chroman-3-acetate
(104) n-butyl 7-[[4-(thiomorpholinoiminomethyl)benzoyl]amino]chroman-3-acetate
(105) 7-[[4-(thiomorpholinoiminomethyl)benzoyl]amino]-1,2,3,4-tetrahydroisoquinoline-2-acetic acid
(106) methyl 7-[[4-(thiomorpholinoiminomethyl)benzoyl]amino]-1,2,3,4-tetrahydroisoquinoline-2-acetate
(107) ethyl 7-[[4-(thiomorpholinoiminomethyl)benzoyl]amino]-1,2,3,4-tetrahydroisoquinoline-2-acetate
(108) 2-hydroxyethyl 7-[[4-(thiomorpholinoiminomethyl)benzoyl]amino]-1,2,3,4-tetrahydroisoquinoline-2-acetate
(109) 2-methoxyethyl 7-[[4-(thiomorpholinoiminomethyl)benzoyl]amino]-1,2,3,4-tetrahydroisoquinoline-2-acetate
(110) n-butyl 7-[[4-(thiomorpholinoiminomethyl)benzoyl]amino]-1,2,3,4-tetrahydroisoquinoline-2-acetate
(111) n-octyl 7-[[4-(thiomorpholinoiminomethyl)benzoyl]amino]-1,2,3,4-tetrahydroisoquinoline-2-acetate
(112) 6-[[4-(thiomorpholinoiminomethyl)benzoyl]amino]-1,2,3,4-tetrahydroisoquinoline-2-acetic acid
(113) methyl 6-[[4-(thiomorpholinoiminomethyl)benzoyl]amino]-1,2,3,4-tetrahydroisoquinoline-2-acetate
(114) ethyl 6-[[4-(thiomorpholinoiminomethyl)benzoyl]amino]-1,2,3,4-tetrahydroisoquinoline-2-acetate
(115) 2-hydroxyethyl 6-[[4-(thiomorpholinoiminomethyl)benzoyl]amino]-1,2,3,4-tetrahydroisoquinoline-2-acetate
(116) 2-methoxyethyl 6-[[4-(thiomorpholinoiminomethyl)benzoyl]amino]-1,2,3,4-tetrahydroisoquinoline-2-acetate
(117) n-butyl 6-[[4-(thiomorpholinoiminomethyl)benzoyl]amino]-1,2,3,4-tetrahydroisoquinoline-2-acetate
(118) 7-[N-[4-(thiomorpholinoiminomethyl)phenyl]carbamoyl]-1,2,3,4-tetrahydronaphthalene-2-acetic acid
(119) ethyl 7-[N-[4-(thiomorpholinoiminomethyl)phenyl]carbamoyl]-1,2,3,4-tetrahydronaphthalene-2-acetate
(120) n-octyl 7-[N-[4-(thiomorpholinoiminomethyl)phenyl]carbamoyl]-1,2,3,4-tetrahydronaphthalene-2-acetate
(121) 6-[N-[4-(thiomorpholinoiminomethyl)phenyl]carbamoyl]-1,2,3,4-tetrahydronaphthalene-2-acetic acid
(122) ethyl 6-[N-[4-(thiomorpholinoiminomethyl)phenyl]carbamoyl]-1,2,3,4-tetrahydronaphthalene-2-acetate
(123) n-butyl 6-[N-[4-(thiomorpholinoiminomethyl)phenyl]carbamoyl]-1,2,3,4-tetrahydronaphthalene-2-acetate
(124) n-octyl 6-[N-[4-(thiomorpholinoiminomethyl)phenyl]carbamoyl]-1,2,3,4-tetrahydronaphthalene-2-acetate
(125) 6-[N-[4-(thiomorpholinoiminomethyl)phenyl]carbamoyl]chroman-3-acetic acid
(126) ethyl 6-[N-[4-(thiomorpholinoiminomethyl)phenyl]carbamoyl]chroman-3-acetate
(127) n-octyl 6-[N-[4-(thiomorpholinoiminomethyl)phenyl]carbamoyl]-chroman-3-acetate
(128) 7-[N-[4-(thiomorpholinoiminomethyl)phenyl]carbamoyl]chroman-3-acetic acid
(129) ethyl 7-[N-[4-(thiomorpholinoiminomethyl)phenyl]carbamoyl]chroman-3-acetate
(130) n-octyl 7-[N-[4-(thiomorpholinoiminomethyl)phenyl]carbamoyl]-chroman-3-acetate
(131) 7-[N-[4-(thiomorpholinoiminomethyl)phenyl]carbamoyl]-1,2,3,4-tetrahydroisoquinoline-2-acetic acid
(132) ethyl 7-[N-[4-(thiomorpholinoiminomethyl)phenyl]carbamoyl]-1,2,3,4-tetrahydroisoquinoline-2-acetate
(133) n-butyl 7-[N-[4-(thiomorpholinoiminomethyl)phenyl]carbamoyl]-1,2,3,4-tetrahydroisoquinoline-2-acetate
(134) 6-[N-[4-(thiomorpholinoiminomethyl)phenyl]carbamoyl]-1,2,3,4-tetrahydroisoquinoline-2-acetic acid
(135) ethyl 6-[N-[4-(thiomorpholinoiminomethyl)phenyl]carbamoyl]-1,2,3,4-tetrahydroisoquinoline-2-acetate
(136) n-butyl 6-[N-[4-(thiomorpholinoiminomethyl)phenyl]carbamoyl]-1,2,3,4-tetrahydroisoquinoline-2-acetate
(137) 7-[[4-(4-methylpiperadinoiminomethyl)benzoyl]amino]-1,2,3,4-tetrahydronaphthalene-2-acetic acid
(138) methyl 7-[[4-(4-methylpiperadinoiminomethyl)benzoyl]amino]-1,2,3,4-tetrahydronaphthalene-2-acetate
(139) ethyl 7-[[4-(4-methylpiperadinoiminomethyl)benzoyl]amino]-1,2,3,4-tetrahydronaphthalene-2-acetate
(140) 2-hydroxyethyl 7-[[4-(4-methylpiperadinoiminomethyl)benzoyl]amino]-1,2,3,4-tetrahydronaphthalene-2-acetate
(141) 2-methoxyethyl 7-[[4-(4-methylpiperadinoiminomethyl)benzoyl]amino]-1,2,3,4-tetrahydronaphthalene-2-acetate
(142) n-butyl 7-[[4-(4-methylpiperadinoiminomethyl)benzoyl]amino]-1,2,3,4-tetrahydronaphthalene-2-acetate
(143) n-octyl 7-[[4-(4-methylpiperadinoiminomethyl)benzoyl]amino]-1,2,3,4-tetrahydronaphthalene-2-acetate
(144) 6-[[4-(4-methylpiperadinoiminomethyl)benzoyl]amino]-1,2,3,4-tetrahydronaphthalene-2-acetic acid
(145) ethyl 6-[[4-(4-methylpiperadinoiminomethyl)benzoyl]amino]-1,2,3,4-tetrahydronaphthalene-2-acetate
(146) n-butyl 6-[[4-(4-methylpiperadinoiminomethyl)benzoyl]amino]-1,2,3,4-tetrahydronaphthalene-2-acetate
(147) 2-methoxyethyl 6-[[4-(4-methylpiperadinoiminomethyl)benzoyl]amino]-1,2,3,4-tetrahydronaphthalene-2-acetate
(148) n-octyl 6-[[4-(4-methylpiperadinoiminomethyl)benzoyl]amino]-1,2,3,4-tetrahydronaphthalene-2-acetate
(149) 6-[[4-(4-methylpiperadinoiminomethyl)benzoyl]amino]chroman-3-acetic acid
(150) methyl 6-[[4-(4-methylpiperadinoiminomethyl)benzoyl]amino]chroman-3-acetate
(151) ethyl 6-[[4-(4-methylpiperadinoiminomethyl)benzoyl]amino]chroman-3-acetate
(152) 2-hydroxyethyl 6-[[4-(4-methylpiperadinoiminomethyl)benzoyl]-amino]chroman-3-acetate
(153) 2-methoxyethyl 6-[[4-(4-methylpiperadinoiminomethyl)benzoyl]-amino]chroman-3-acetate
(154) n-butyl 6-[[4-(4-methylpiperadinoiminomethyl)benzoyl]amino]chroman-3-acetate
(155) n-octyl 6-[[4-(4-methylpiperadinoiminomethyl)benzoyl]amino]chroman-3-acetate
(156) 7-[[4-(4-methylpiperadinoiminomethyl)benzoyl]amino]chroman-3-acetic acid (157) methyl 7-[[4-(4-methylpiperadinoiminomethyl) benzoyl]amino]chroman-3-acetate
(158) ethyl 7-[[4-(4-methylpiperadinoiminomethyl) benzoyl]amino]chroman-3-acetate
(159) 2-hydroxyethyl 7-[[4-(4-methylpiperadinoiminomethyl)benzoyl]-amino]chroman-3-acetate
(160) 2-methoxyethyl 7-[[4-(4-methylpiperadinoiminomethyl)benzoyl]-amino]chroman-3-acetate
(161) n-butyl 7-[[4-(4-methylpiperadinoiminomethyl) benzoyl]amino]chroman-3-acetate
(162) n-octyl 7-[[4-(4-methylpiperadinoiminomethyl) benzoyl]amino]chroman-3-acetate
(163) 7-[[4-(4-methylpiperadinoiminomethyl)benzoyl] amino]-1,2,3,4-tetrahydroisoquinoline-2-acetic acid
(164) methyl 7-[[4-(4-methylpiperadinoiminomethyl) benzoyl]amino]-1,2,3,4-tetrahydroisoquinoline-2-acetate
(165) ethyl 7-[[4-(4-methylpiperadinoiminomethyl) benzoyl]amino]-1,2,3,4-tetrahydroisoquinoline-2-acetate
(166) 2-hydroxyethyl 7-[[4-(4-methylpiperadinoiminomethyl)benzoyl]amino]-1,2,3,4-tetrahydroisoquinoline-2-acetate
(167) 2-methoxyethyl 7-[[4-(4-methylpiperadinoiminomethyl)benzoyl]amino]-1,2,3,4-tetrahydroisoquinoline-2-acetate
(168) n-butyl 7-[[4-(4-methylpiperadinoiminomethyl) benzoyl]amino]-1,2,3,4-tetrahydroisoquinoline-2-acetate
(169) n-octyl 7-[[4-(4-methylpiperadinoiminomethyl) benzoyl]amino]-1,2,3,4-tetrahydroisoquinoline-2-acetate
(170) 6-[[4-(4-methylpiperadinoiminomethyl)benzoyl] amino]-1,2,3,4-tetrahydroisoquinoline-2-acetic acid
(171) ethyl 6-[[4-(4-methylpiperadinoiminomethyl) benzoyl]amino]-1,2,3,4-tetrahydroisoquinoline-2-acetate
(172) n-propyl 6-[[4-(4-methylpiperadinoiminomethyl) benzoyl]amino]-1,2,3,4-tetrahydroisoquinoline-2-acetate
(173) 2-methoxyethyl 6-[[4-(4-methylpiperadinoiminomethyl)benzoyl]amino]-1,2,3,4-tetrahydroisoquinoline-2-acetate
(174) n-butyl 6-[[4-(4-methylpiperadinoiminomethyl) benzoyl]amino]-1,2,3,4-tetrahydroisoquinoline-2-acetate
(175) n-octyl 6-[[4-(4-methylpiperadinoiminomethyl) benzoyl]amino]-1,2,3,4-tetrahydroisoquinoline-2-acetate
(176) 7-[N-[4-(4-methylpiperadinoiminomethyl)phenyl] carbamoyl]-1,2,3,4-tetrahydronaphthalene-2-acetic acid
(177) ethyl 7-[N-[4-(4-methylpiperadinoiminomethyl) phenyl]carbamoyl]-1,2,3,4-tetrahydronaphthalene-2-acetate
(178) n-octyl 7-[N-[4-(4-methylpiperadinoiminomethyl) phenyl]carbamoyl]-1,2,3,4-tetrahydronaphthalene-2-acetate
(179) 6-[N-[4-(4-methylpiperadinoiminomethyl)phenyl] carbamoyl]-1,2,3,4-tetrahydronaphthalene-2-acetic acid
(180) ethyl 6-[N-[4-(4-methylpiperadinoiminomethyl) phenyl]carbamoyl]-1,2,3,4-tetrahydronaphthalene-2-acetate
(181) n-octyl 6-[N-[4-(4-methylpiperadinoiminomethyl) phenyl]carbamoyl]-1,2,3,4-tetrahydronaphthalene-2-acetate
(182) 6-[N-[4-(4-methylpiperadinoiminomethyl)phenyl] carbamoyl]chroman-3-acetic acid
(183) ethyl 6-[N-[4-(4-methylpiperadinoiminomethyl) phenyl]carbamoyl]-chroman-3-acetate
(184) n-octyl 6-[N-[4-(4-methylpiperadinoiminomethyl) phenyl]carbamoyl]-chroman-3-acetate
(185) 7-[N-[4-(4-methylpiperadinoiminomethyl)phenyl] carbamoyl]chroman-3-acetic acid
(186) ethyl 7-[N-[4-(4-methylpiperadinoiminomethyl) phenyl]carbamoyl]-chroman-3-acetate
(187) n-octyl 7-[N-[4-(4-methylpiperadinoiminomethyl) phenyl]carbamoyl]-chroman-3-acetate
(188) 7-[N-[4-(4-methylpiperadinoiminomethyl)phenyl] carbamoyl]-1,2,3,4-tetrahydroisoquinoline-2-acetic acid
(189) ethyl 7-[N-[4-(4-methylpiperadinoiminomethyl) phenyl]carbamoyl]-1,2,3,4-tetrahydroisoquinoline-2-acetate
(190) n-butyl 7-[N-[4-(4-methylpiperadinoiminomethyl) phenyl]carbamoyl]-1,2,3,4-tetrahydroisoquinoline-2-acetate
(191) 6-[N-[4-(4-methylpiperadinoiminomethyl)phenyl] carbamoyl]-1,2,3,4-tetrahydroisoquinoline-2-acetic acid
(192) ethyl 6-[N-[4-(4-methylpiperadinoiminomethyl) phenyl]carbamoyl]-1,2,3,4-tetrahydroisoquinoline-2-acetate
(193) n-octyl 6-[N-[4-(4-methylpiperadinoiminomethyl) phenyl]carbamoyl]-1,2,3,4-tetrahydroisoquinoline-2-acetate
(194) 7-[[4-(piperidinoiminomethyl)benzoyl]amino]-1,2,3,4-tetrahydronaphthalene-2-acetic acid
(195) methyl 7-[[4-(piperidinoiminomethyl)benzoyl]amino]-1,2,3,4-tetrahydronaphthalene-2-acetate
(196) ethyl 7-[[4-(piperidinoiminomethyl)benzoyl]amino]-1,2,3,4-tetrahydronaphthalene-2-acetate
(197) n-butyl 7-[[4-(piperidinoiminomethyl)benzoyl]amino]-1,2,3,4-tetrahydronaphthalene-2-acetate
(198) 2-hydroxyethyl 7-[[4-(piperidinoiminomethyl) benzoyl]amino]-1,2,3,4-tetrahydronaphthalene-2-acetate
(199) 2-methoxyethyl 7-[[4-(piperidinoiminomethyl) benzoyl]amino]-1,2,3,4-tetrahydronaphthalene-2-acetate
(200) n-octyl 7-[[4-(piperidinoiminomethyl)benzoyl]amino]-1,2,3,4-tetrahydronaphthalene-2-acetate
(201) 6-[[4-(piperidinoiminomethyl)benzoyl]amino]-1,2,3,4-tetrahydronaphthalene-2-acetic acid
(202) methyl 6-[[4-(piperidinoiminomethyl)benzoyl]amino]-1,2,3,4-tetrahydronaphthalene-2-acetate
(203) ethyl 6-[[4-(piperidinoiminomethyl)benzoyl]amino]-1,2,3,4-tetrahydronaphthalene-2-acetate
(204) n-butyl 6-[[4-(piperidinoiminomethyl)benzoyl]amino]-1,2,3,4-tetrahydronaphthalene-2-acetate
(205) 2-hydroxyethyl 6-[[4-(piperidinoiminomethyl) benzoyl]amino]- 1,2,3,4-tetrahydronaphthalene-2-acetate
(206) 2-methoxyethyl 6-[[4-(piperidinoiminomethyl) benzoyl]amino]-1,2,3,4-tetrahydronaphthalene-2-acetate
(207) 6-[[4-(piperidinoiminomethyl)benzoyl]amino] chroman-3-acetic acid
(208) methyl 6-[[4-(piperidinoiminomethyl)benzoyl]amino] chroman-3-acetate
(209) ethyl 6-[[4-(piperidinoiminomethyl)benzoyl]amino] chroman-3-acetate
(210) n-butyl 6-[[4-(piperidinoiminomethyl)benzoyl]amino] chroman-3-acetate
(211) 2-hydroxyethyl 6-[[4-(piperidinoiminomethyl) benzoyl]amino]chroman-3-acetate
(212) 2-methoxyethyl 6-[[4-(piperidinoiminomethyl) benzoyl]amino]chroman-3-acetate
(213) n-octyl 6-[[4-(piperidinoiminomethyl)benzoyl]amino] chroman-3-acetate
(214) 7-[[4-(piperidinoiminomethyl)benzoyl]amino] chroman-3-acetic acid
(215) ethyl 7-[[4-(piperidinoiminomethyl)benzoyl]amino] chroman-3-acetate
(216) n-butyl 7-[[4-(piperidinoiminomethyl)benzoyl]amino] chroman-3-acetate
(217) 2-methoxyethyl 7-[[4-(piperidinoiminomethyl) benzoyl]amino]chroman-3-acetate (218) n-octyl 7-[[4-(piperidinoiminomethyl)benzoyl]amino] chroman-3-acetate
(219) 7-[[4-(piperidinoiminomethyl)benzoyl]amino]-1,2,3,4-tetrahydroisoquinoline-2-acetic acid
(220) methyl 7-[[4-(piperidinoiminomethyl)benzoyl]amino]-1,2,3,4-tetrahydroisoquinoline-2-acetate
(221) ethyl 7-[[4-(piperidinoiminomethyl)benzoyl]amino]-1,2,3,4-tetrahydroisoquinoline-2-acetate
(222) n-butyl 7-[[4-(piperidinoiminomethyl)benzoyl]amino]-1,2,3,4-tetrahydroisoquinoline- 2-acetate
(223) 2-hydroxyethyl 7-[[4-(piperidinoiminomethyl)benzoyl]amino]-1,2,3,4-tetrahydroisoquinoline-2-acetate
(224) 2-methoxyethyl 7-[[4-(piperidinoiminomethyl)benzoyl]amino]-1,2,3,4-tetrahydroisoquinoline-2-acetate
(225) n-octyl 7-[[4-(piperidinoiminomethyl)benzoyl]amino]-1,2,3,4-tetrahydroisoquinoline-2-acetate
(226) 6-[[4-(piperidinoiminomethyl)benzoyl]amino]-1,2,3,4-tetrahydroisoquinoline-2-acetic acid
(227) ethyl 6-[[4-(piperidinoiminomethyl)benzoyl]amino]-1,2,3,4-tetrahydroisoquinoline-2-acetate
(228) n-butyl 6-[[4-(piperidinoiminomethyl)benzoyl]amino]-1,2,3,4-tetrahydroisoquinoline-2-acetate
(229) 2-methoxyethyl 6-[[4-(piperidinoiminomethyl)benzoyl]amino]-1,2,3,4-tetrahydroisoquinoline-2-acetate
(230) n-octyl 6-[[4-(piperidinoiminomethyl)benzoyl]amino]-1,2,3,4-tetrahydroisoquinoline-2-acetate
(231) 7-[N-[4-(piperidinoiminomethyl)phenyl]carbamoyl]-1,2,3,4-tetrahydronaphthalene-2-acetic acid
(232) ethyl 7-[N-[4-(piperidinoiminomethyl)phenyl]carbamoyl]-1,2,3,4-tetrahydronaphthalene-2-acetate
(233) n-butyl 7-[N-[4-(piperidinoiminomethyl)phenyl]carbamoyl]-1,2,3,4-tetrahydronaphthalene-2-acetate
(234) 6-[N-[4-(piperidinoiminomethyl)phenyl]carbamoyl]-1,2,3,4-tetrahydronaphthalene-2-acetic acid
(235) ethyl 6-[N-[4-(piperidinoiminomethyl)phenyl]carbamoyl]-1,2,3,4-tetrahydronaphthalene-2-acetate
(236) n-butyl 6-[N-[4-(piperidinoiminomethyl)phenyl]carbamoyl]-1,2,3,4-tetrahydronaphthalene-2-acetate
(237) 6-[N-[4-(piperidinoiminomethyl)phenyl]carbamoyl] chroman-3-acetic acid
(238) ethyl 6-[N-[4-(piperidinoiminomethyl)phenyl]carbamoyl]chroman-3-acetate
(239) n-octyl 6-[N-[4-(piperidinoiminomethyl)phenyl]carbamoyl]chroman-3-acetate
(240) 7-[N-[4-(piperidinoiminomethyl)phenyl]carbamoyl]chroman-3-acetic acid
(241) ethyl 7-[N-[4-(piperidinoiminomethyl)phenyl]carbamoyl]chroman-3-acetate
(242) n-octyl 7-[N-[4-(piperidinoiminomethyl)phenyl]carbamoyl]chroman-3-acetate
(243) 7-[N-[4-(piperidinoiminomethyl)phenyl]carbamoyl]-1,2,3,4-tetrahydroisoquinoline-2-acetic acid
(244) methyl 7-[N-[4-(piperidinoiminomethyl)phenyl]carbamoyl]-1,2,3,4-tetrahydroisoquinoline-2-acetate
(245) 2-hydroxyethyl 7-[N-[4-(piperidinoiminomethyl)phenyl]carbamoyl]-1,2,3,4-tetrahydroisoquinoline-2-acetate
(246) 6-[N-[4-(piperidinoiminomethyl)phenyl]carbamoyl]-1,2,3,4-tetrahydroisoquinoline-2-acetic acid
(247) ethyl 6-[N-[4-(piperidinoiminomethyl)phenyl]carbamoyl]-1,2,3,4-tetrahydroisoquinoline-2-acetate
(248) 2-methoxyethyl 6-[N-[4-(piperidinoiminomethyl)phenyl]carbamoyl]-1,2,3,4-tetrahydroisoquinoline-2-acetate
(249) 7-[[4-(pyrrolidinoiminomethyl)benzoyl]amino]-1,2,3,4-tetrahydronaphthalene-2-acetic acid
(250) ethyl 7-[[4-(pyrrolidinoiminomethyl)benzoyl]amino]-1,2,3,4-tetrahydronaphthalene-2-acetate
(251) 6-[[4-(pyrrolidinoiminomethyl)benzoyl]amino]-1,2,3,4-tetrahydronaphthalene- 2-acetic acid
(252) ethyl 6-[[4-(pyrrolidinoiminomethyl)benzoyl]amino]-1,2,3,4-tetrahydronaphthalene-2-acetate
(253) 7-[[4-(homopiperidinoiminomethyl)benzoyl]amino]-1,2,3,4-tetrahydronaphthalene-2-acetic acid
(254) ethyl 7-[[4-(homopiperidinoiminomethyl)benzoyl]amino]-1,2,3,4-tetrahydronaphthalene-2-acetate
(255) 6-[[4-(homopiperidinoiminomethyl)benzoyl]amino]-1,2,3,4-tetrahydronaphthalene-2-acetic acid
(256) ethyl 6-[[4-(homopiperidinoiminomethyl)benzoyl]amino]-1,2,3,4-tetrahydronaphthalene-2-acetate
(257) ethyl 7-[[4-($N^1$-propargylamidino)benzoyl]amino]-1,2,3,4-tetrahydronaphthalene-2-acetate
(258) 7-[[4-($N^2$-propargylamidino)benzoyl]amino]-1,2,3,4-tetrahydronaphthalene-2-acetic acid
(259) methyl 7-[[4-($N^2$-propargylamidino)benzoyl]amino]-1,2,3,4-tetrahydronaphthalene-2-acetate
(260) ethyl 7-[[4-($N^2$-propargylamidino)benzoyl]amino]-1,2,3,4-tetrahydronaphthalene-2-acetate
(261) n-butyl 7-[[4-($N^2$-propargylamidino)benzoyl]amino]-1,2,3,4-tetrahydronaphthalene-2-acetate
(262) 2-hydroxyethyl 7-[[4-($N^2$-propargylamidino)benzoyl]amino]-1,2,3,4-tetrahydronaphthalene-2-acetate
(263) 2-methoxyethyl 7-[[4-($N^2$-propargylamidino)benzoyl]amino]-1,2,3,4-tetrahydronaphthalene-2-acetate
(264) n-octyl 7-[[4-($N^2$-propargylamidino)benzoyl]amino]-1,2,3,4-tetrahydronaphthalene-2-acetate
(265) 6-[[4-($N^2$-propargylamidino)benzoyl]amino]-1,2,3,4-tetrahydronaphthalene-2-acetic acid
(266) ethyl 6-[[4-($N^2$-propargylamidino)benzoyl]amino]-1,2,3,4-tetrahydronaphthalene-2-acetate
(267) n-butyl 6-[[4-($N^2$-propargylamidino)benzoyl]amino]-1,2,3,4-tetrahydronaphthalene-2-acetate
(268) 2-hydroxyethyl 6-[[4-($N^2$-propargylamidino)benzoyl]amino]-1,2,3,4-tetrahydronaphthalene-2-acetate
(269) 2-methoxyethyl 6-[[4-($N^2$-propargylamidino)benzoyl]amino]-1,2,3,4-tetrahydronaphthalene-2-acetate
(270) n-octyl 6-[[4-($N^2$-propargylamidino)benzoyl]amino]-1,2,3,4-tetrahydronaphthalene-2-acetate
(271) 6-[[4-($N^2$-propargylamidino)benzoyl]amino] chroman-3-acetic acid
(272) ethyl 6-[[4-($N^2$-propargylamidino)benzoyl]amino] chroman-3-acetate
(273) n-butyl 6-[[4-($N^2$-propargylamidino)benzoyl]amino] chroman-3-acetate
(274) 2-hydroxyethyl 6-[[4-($N^2$-propargylamidino)benzoyl]amino]chroman-3-acetate
(275) 2-methoxyethyl 6-[[4-($N^2$-propargylamidino)benzoyl]amino]chroman-3-acetate
(276) n-octyl 6-[[4-($N^2$-propargylamidino)benzoyl]amino] chroman-3-acetate
(277) 7-[[4-($N^2$-propargylamidino)benzoyl]amino] chroman-3-acetic acid
(278) ethyl 7-[[4-($N^2$-propargylamidino)benzoyl]amino] chroman-3-acetate
(279) n-butyl 7-[[4-($N^2$-propargylamidino)benzoyl]amino] chroman-3-acetate
(280) 2-hydroxyethyl 7-[[4-($N^2$-propargylamidino)benzoyl]amino]chroman-3-acetate
(281) 2-methoxyethyl 7-[[4-($N^2$-propargylamidino)benzoyl]amino]chroman-3-acetate
(282) n-octyl 7-[[4-($N^2$-propargylamidino)benzoyl]amino] chroman-3-acetate
(283) 7-[[4-($N^2$-propargylamidino)benzoyl]amino]-1,2,3,4-tetrahydroisoquinoline-2-acetic acid
(284) ethyl 7-[[4-($N^2$-propargylamidino)benzoyl]amino]-1,2,3,4-tetrahydroisoquinoline- 2-acetate (285) n-butyl 7-[[4-(N²-propargylamidino)benzoyl]amino]-1,2,3,4-tetrahydroisoquinoline-2-acetate
(286) 2-hydroxyethyl 7-[[4-(N²-propargylamidino)benzoyl]amino]-1,2,3,4-tetrahydroisoquinoline-2-acetate
(287) 2-methoxyethyl 7-[[4-(N²-propargylamidino)benzoyl]amino]-1,2,3,4-tetrahydroisoquinoline-2-acetate
(288) n-octyl 7-[[4-(N²-propargylamidino)benzoyl]amino]-1,2,3,4-tetrahydroisoquinoline-2-acetate
(289) 6-[[4-(N²-propargylamidino)benzoyl]amino]-1,2,3,4-tetrahydroisoquinoline-2-acetic acid
(290) ethyl 6-[[4-(N²-propargylamidino)benzoyl]amino]-1,2,3,4-tetrahydroisoquinoline-2-acetate
(291) n-butyl 6-[[4-(N²-propargylamidino)benzoyl]amino]-1,2,3,4-tetrahydroisoquinoline-2-acetate
(292) 2-hydroxyethyl 6-[[4-(N²-propargylamidino)benzoyl]amino]-1,2,3,4-tetrahydroisoquinoline-2-acetate
(293) 2-methoxyethyl 6-[[4-(N²-propargylamidino)benzoyl]amino]-1,2,3,4-tetrahydroisoquinoline-2-acetate
(294) n-octyl 6-[[4-(N²-propargylamidino)benzoyl]amino]-1,2,3,4-tetrahydroisoquinoline-2-acetate
(295) ethyl 7-[N-[4-(N²-propargylamidino)phenyl]carbamoyl]-1,2,3,4-tetrahydronaphthalene-2-acetate
(296) ethyl 6-[N-[4-(N²-propargylamidino)phenyl]carbamoyl]-1,2,3,4-tetrahydronaphthalene-2-acetate
(297) ethyl 6-[N-[4-(N²-propargylamidino)phenyl]carbamoyl]chroman-3-acetate
(298) ethyl 7-[N-[4-(N²-propargylamidino)phenyl]carbamoyl]chroman-3-acetate
(299) ethyl 7-[N-[4-(N²-propargylamidino)phenyl]carbamoyl]-1,2,3,4-tetrahydroisoquinoline-2-acetate
(300) ethyl 6-[N-[4-(N²-propargylamidino)phenyl]carbamoyl]-1,2,3,4-tetrahydroisoquinoline-2-acetate
(301) 7-[[4-[N²-(2-furfuryl)amidino]benzoyl]amino]-1,2,3,4-tetrahydronaphthalene-2-acetic acid
(302) methyl 7-[[4-[N²-(2-furfuryl)amidino]benzoyl]amino]-1,2,3,4-tetrahydronaphthalene-2-acetate
(303) ethyl 7-[[4-[N²-(2-furfuryl)amidino]benzoyl]amino]-1,2,3,4-tetrahydronaphthalene-2-acetate
(304) n-butyl 7-[[4-[N²-(2-furfuryl)amidino]benzoyl]amino]-1,2,3,4-tetrahydronaphthalene-2-acetate
(305) 2-hydroxyethyl 7-[[4-[N²-(2-furfuryl)amidino]benzoyl]amino]-1,2,3,4-tetrahydronaphthalene-2-acetate
(306) 2-methoxyethyl 7-[[4-[N²-(2-furfuryl)amidino]benzoyl]amino]-1,2,3,4-tetrahydronaphthalene-2-acetate
(307) n-octyl 7-[[4-[N²-(2-furfuryl)amidino]benzoyl]amino]-1,2,3,4-tetrahydronaphthalene-2-acetate
(308) 6-[[4-[N²-(2-furfuryl)amidino]benzoyl]amino]-1,2,3,4-tetrahydronaphthalene-2-acetic acid
(309) ethyl 6-[[4-[N²-(2-furfuryl)amidino]benzoyl]amino]-1,2,3,4-tetrahydronaphthalene-2-acetate
(310) n-butyl 6-[[4-[N²-(2-furfuryl)amidino]benzoyl]amino]-1,2,3,4-tetrahydronaphthalene-2-acetate
(311) 2-hydroxyethyl 6-[[4-[N²-(2-furfuryl)amidino]benzoyl]amino]-1,2,3,4-tetrahydronaphthalene-2-acetate
(312) 2-methoxyethyl 6-[[4-[N²-(2-furfuryl)amidino]benzoyl]amino]-1,2,3,4-tetrahydronaphthalene-2-acetate
(313) n-octyl 6-[[4-[N²-(2-furfuryl)amidino]benzoyl]amino]-1,2,3,4-tetrahydronaphthalene-2-acetate
(314) 6-[[4-[N¹-(2-furfuryl)amidino]benzoyl]amino]chroman-3-acetic acid
(315) methyl 6-[[4-[N²-(2-furfuryl)amidino]benzoyl]amino]croman-3-acetate
(316) ethyl 6-[[4-[N²-(2-furfuryl)amidino]benzoyl]amino]chroman-3-acetate
(317) n-butyl 6-[[4-[N²-(2-furfuryl)amidino]benzoyl]amino]chroman-3-acetate
(318) 2-hydroxyethyl 6-[[4-[N²-(2-furfuryl)amidino]benzoyl]amino]chroman-3-acetate
(319) 2-methoxyethyl 6-[[4-[N²-(2-furfuryl)amidino]benzoyl]amino]chroman-3-acetate
(320) n-octyl 6-[[4-[N²-(2-furfuryl)amidino]benzoyl]amino]chroman-3-acetate
(321) 7-[[4-[N²-(2-furfuryl)amidino]benzoyl]amino]chroman-3-acetic acid
(322) methyl 7-[[4-[N²-(2-furfuryl)amidino]benzoyl]amino]chroman-3-acetate
(323) ethyl 7-[[4-[N²-(2-furfuryl)amidino]benzoyl]amino]chroman-3-acetate
(324) n-butyl 7-[[4-[N²-(2-furfuryl)amidino]benzoyl]amino]chroman-3-acetate
(325) 7-[[4-[N²-(2-furfuryl)amidino]benzoyl]amino]-1,2,3,4-tetrahydroisoquinoline-2-acetic acid
(326) methyl 7-[[4-[N²-(2-furfuryl)amidino]benzoyl]amino]-1,2,3,4-tetrahydroisoquinoline-2-acetate
(327) ethyl 7-[[4-[N²-(2-furfuryl)amidino]benzoyl]amino]-1,2,3,4-tetrahydroisoquinoline-2-acetate
(328) n-butyl 7-[[4-[N²-(2-furfuryl)amidino]benzoyl]amino]-1,2,3,4-tetrahydroisoquinoline-2-acetate
(329) 2-hydroxyethyl 7-[[4-[N²-(2-furfuryl)amidino]benzoyl]amino]-1,2,3,4-tetrahydroisoquinoline-2-acetate
(330) 2-methoxyethyl 7-[[4-[N²-(2-furfuryl)amidino]benzoyl]amino]-1,2,3,4-tetrahydroisoquinoline-2-acetate
(331) n-octyl 7-[[4-[N²-(2-furfuryl)amidino]benzoyl]amino]-1,2,3,4-tetrahydroisoquinoline-2-acetate
(332) 6-[[4-[N²-(2-furfuryl)amidino]benzoyl]amino]-1,2,3,4-tetrahydroisoquinoline-2-acetic acid
(333) methyl 6-[[4-[N²-(2-furfuryl)amidino]benzoyl]amino]-1,2,3,4-tetrahydroisoquinoline-2-acetate
(334) ethyl 6-[[4-[N²-(2-furfuryl)amidino]benzoyl]amino]-1,2,3,4-tetrahydroisoquinoline-2-acetate
(335) n-butyl 6-[[4-[N²-(2-furfuryl)amidino]benzoyl]amino]-1,2,3,4-tetrahydroisoquinoline-2-acetate
(336) 2-methoxyethyl 6-[[4-[N²-(2-furfuryl)amidino]benzoyl]amino]-1,2,3,4-tetrahydroisoquinoline-2-acetate
(337) n-octyl 6-[[4-[N²-(2-furfuryl)amidino]benzoyl]amino]-1,2,3,4-tetrahydroisoquinoline-2-acetate
(338) ethyl 7-[N-[4-[N²-(2-furfuryl)amidino]phenyl]carbamoyl]-1,2,3,4-tetrahydronaphthalene-2-acetate
(339) ethyl 6-[N-[4-[N²-(2-furfuryl)amidino]phenyl]carbamoyl]-1,2,3,4-tetrahydronaphthalene-2-acetate
(340) ethyl 6-[N-[4-[N²-(2-furfuryl)amidino]phenyl]carbamoyl]chroman-3-acetate
(341) ethyl 7-[N-[4-[N²-(2-furfuryl)amidino]phenyl]carbamoyl]chroman-3-acetate
(342) ethyl 7-[N-[4-[N²-(2-furfuryl)amidino]phenyl]carbamoyl]-1,2,3,4-tetrahydroisoquinoline-2-acetate
(343) ethyl 6-[N-[4-[N²-(2-furfuryl)amidino]phenyl]carbamoyl]-1,2,3,4-tetrahydroisoquinoline-2-acetate
(344) 7-[[4-(N¹-methyl-N¹-propargylamidino)benzoyl]amino]-1,2,3,4-tetrahydronaphthalene-2-acetic acid
(345) methyl 7-[[4-(N¹-methyl-N¹-propargylamidino)benzoyl]amino]-1,2,3,4-tetrahydronaphthalene-2-acetate
(346) ethyl 7-[[4-(N¹-methyl-N¹-propargylamidino)benzoyl]amino]-1,2,3,4-tetrahydronaphthalene-2-acetate
(347) n-butyl 7-[[4-(N¹-methyl-N¹-propargylamidino)benzoyl]amino]-1,2,3,4-tetrahydronaphthalene-2-acetate
(348) 2-hydroxyethyl 7-[[4-(N¹-methyl-N¹-propargylamidino)benzoyl]amino]-1,2,3,4-tetrahydronaphthalene-2-acetate
(349) 2-methoxyethyl 7-[[4-(N¹-methyl-N¹-propargylamidino)benzoyl]amino]-1,2,3,4-tetrahydronaphthalene-2-acetate
(350) n-octyl 7-[[4-(N¹-methyl-N¹-propargylamidino)benzoyl]amino]-1,2,3,4-tetrahydronaphthalene-2-acetate
(351) 6-[[4-(N¹-methyl-N¹-propargylamidino)benzoyl]amino]-1,2,3,4-tetrahydronaphthalene-2-acetic acid (352) methyl 6-[[4-($N^1$-methyl-$N^1$-propargylamidino)benzoyl]amino]-1,2,3,4-tetrahydronaphthalene-2-acetate
(353) ethyl 6-[[4-($N^1$-methyl-$N^1$-propargylamidino)benzoyl]amino]-1,2,3,4-tetrahydronaphthalene-2-acetate
(354) n-butyl 6-[[4-($N^1$-methyl-$N^1$-propargylamidino)benzoyl]amino]-1,2,3,4-tetrahydronaphthalene-2-acetate
(355) 6-[[4-($N^1$-methyl-$N^1$-propargylamidino]benzoyl)amino]chroman-3-acetic acid
(356) methyl 6-[[4-($N^1$-methyl-$N^1$-propargylamidino)benzoyl]amino]chroman-3-acetate
(357) ethyl 6-[[4-($N^1$-methyl-$N^1$-propargylamidino)benzoyl]amino]chroman-3-acetate
(358) n-butyl 6-[[4-($N^1$-methyl-$N^1$-propargylamidino)benzoyl]amino]chroman-3-acetate
(359) 2-hydroxyethyl 6-[[4-($N^1$-methyl-$N^1$-propargylamidino)benzoyl]amino]chroman-3-acetate
(360) 2-methoxyethyl 6-[[4-($N^1$-methyl-$N^1$-propargylamidino)benzoyl]amino]chroman-3-acetate
(361) n-octyl 6-[[4-($N^1$-methyl-$N^1$-propargylamidino]benzoyl)amino]chroman-3-acetate
(362) 7-[[4-($N^1$-methyl-$N^1$-propargylamidino)benzoyl]amino]chroman-3-acetic acid
(363) ethyl 7-[[4-($N^1$-methyl-$N^1$-propargylamidino)benzoyl]amino]chroman-3-acetate
(364) n-butyl 7-[[4-($N^1$-methyl-$N^1$-propargylamidino)benzoyl]amino]chroman-3-acetate
(365) 7-[[4-($N^1$-methyl-$N^1$-propargylamidino)benzoyl]amino]-1,2,3,4-tetrahydroisoquinoline-2-acetic acid
(366) methyl 7-[[4-($N^1$-methyl-$N^1$-propargylamidino)benzoyl]amino]-1,2,3,4-tetrahydroisoquinoline-2-acetate
(367) ethyl 7-[[4-($N^1$-methyl-$N^1$-propargylamidino)benzoyl]amino]-1,2,3,4-tetrahydroisoquinoline-2-acetate
(368) n-butyl 7-[[4-($N^1$-methyl-$N^1$-propargylamidino)benzoyl]amino]-1,2,3,4-tetrahydroisoquinoline-2-acetate
(369) 2-hydroxyethyl 7-[[4-($N^1$-methyl-$N^1$-propargylamidino)benzoyl]amino]-1,2,3,4-tetrahydroisoquinoline-2-acetate
(370) 2-methoxyethyl 7-[[4-($N^1$-methyl-$N^1$-propargylamidino)benzoyl]amino]-1,2,3,4-tetrahydroisoquinoline-2-acetate
(371) n-octyl 7-[[4-($N^1$-methyl-$N^1$-propargylamidino)benzoyl]amino]-1,2,3,4-tetrahydroisoquinoline-2-acetate
(372) 6-[[4-($N^1$-methyl-$N^1$-propargylamidino)benzoyl]amino]-1,2,3,4-tetrahydroisoquinoline- 2-acetic acid
(373) ethyl 6-[[4-($N^1$-methyl-$N^1$-propargylamidino)benzoyl]amino]-1,2,3,4-tetrahydroisoquinoline-2-acetate
(374) n-butyl 6-[[4-($N^1$-methyl-$N^1$-propargylamidino)benzoyl]amino]-1,2,3,4-tetrahydroisoquinoline-2-acetate
(375) 2-methoxyethyl 6-[[4-($N^1$-methyl-$N^1$-propargylamidino)benzoyl]amino]-1,2,3,4-tetrahydroisoquinoline-2-acetate
(376) n-octyl 6-[[4-($N^1$-methyl-$N^1$-propargylamidino)benzoyl]amino]-1,2,3,4-tetrahydroisoquinoline-2-acetate
(377) ethyl 7-[N-[4-($N^1$-methyl-$N^1$-propargylamidino)phenyl]carbamoyl]-1,2,3,4-tetrahydronaphthalene-2-acetate
(378) ethyl 6-[N-[4-($N^1$-methyl-$N^1$-propargylamidino)phenyl]carbamoyl]-1,2,3,4-tetrahydronaphthalene-2-acetate
(379) ethyl 6-[N-[4-($N^1$-methyl-$N^1$-propargylamidino)phenyl]carbamoyl]chroman-3-acetate
(380) ethyl 7-[N-[4-($N^1$-methyl-$N^1$-propargylamidino)phenyl]carbamoyl]chroman-3-acetate
(381) ethyl 7-[N-[4-($N^1$-methyl-$N^1$-propargylamidino)phenyl]carbamoyl]-1,2,3,4-tetrahydroisoquinoline-2-acetate
(382) ethyl 6-[N-[4-($N^1$-methyl-$N^1$-propargylamidino)phenyl]carbamoyl]-1,2,3,4-tetrahydroisoquinoline-2-acetate
(383) 7-[[4-[$N^2$-(2-thenyl)amidino]benzoyl]amino]-1,2,3,4-tetrahydronaphthalene-2-acetic acid
(384) ethyl 7-[[4-[$N^2$-(2-thenyl)amidino]benzoyl]amino]-1,2,3,4-tetrahydronaphthalene-2-acetate
(385) 6-[[4-[$N^2$-(2-thenyl)amidino]benzoyl]amino]-1,2,3,4-tetrahydronaphthalene-2-acetic acid
(386) ethyl 6-[[4-[$N^2$-(2-thenyl)amidino]benzoyl]amino]-1,2,3,4-tetrahydronaphthalene-2-acetate
(387) 7-[[4-[$N^2$-(2-picolyl)amidino]benzoyl]amino]-1,2,3,4-tetrahydronaphthalene-2-acetic acid
(388) ethyl 7-[[4-[$N^2$-(2-picolyl)amidino]benzoyl]amino]-1,2,3,4-tetrahydronaphthalene-2-acetate
(389) 6-[[4-[$N^2$-(2-picolyl)amidino]benzoyl]amino]-1,2,3,4-tetrahydronaphthalene-2-acetic acid
(390) ethyl 6-[[4-[$N^2$-(2-picolyl)amidino]benzoyl]amino]-1,2,3,4-tetrahydronaphthalene-2-acetate
(391) 7-[[4-[$N^2$-(3-picolyl)amidino]benzoyl]amino]-1,2,3,4-tetrahydronaphthalene-2-acetic acid
(392) ethyl 7-[[4-[$N^2$-(3-picolyl)amidino]benzoyl]amino]-1,2,3,4-tetrahydronaphthalene-2-acetate
(393) 6-[[4-[$N^2$-(3-picolyl)amidino]benzoyl]amino]-1,2,3,4-tetrahydronaphthalene-2-acetic acid
(394) ethyl 6-[[4-[$N^2$-(3-picolyl)amidino]benzoyl]amino]-1,2,3,4-tetrahydronaphthalene-2-acetate
(395) 7-[[4-[$N^2$-(4-picolyl)amidino]benzoyl]amino]-1,2,3,4-tetrahydronaphthalene-2-acetic acid
(396) ethyl 7-[[4-[$N^2$-(4-picolyl)amidino]benzoyl]amino]-1,2,3,4-tetrahydronaphthalene-2-acetate
(397) 6-[[4-[$N^2$-(4-picolyl)amidino]benzoyl]amino]-1,2,3,4-tetrahydronaphthalene-2-acetic acid
(398) ethyl 6-[[4-[$N^2$-(4-picolyl)amidino]benzoyl]amino]-1,2,3,4-tetrahydronaphthalene-2-acetate
(399) 7-[[4-[$N^2$-[2-(4-pyridyl)ethyl]amidino]benzoyl]amino]-1,2,3,4-tetrahydronaphthalene-2-acetic acid
(400) ethyl 7-[[4-[$N^2$-[2-(4-pyridyl)ethyl]amidino]benzoyl]amino]-1,2,3,4-tetrahydronaphthalene-2-acetate
(401) ethyl 7-[[4-(4-phenylpiperadinoiminomethyl)benzoyl]amino]-1,2,3,4-tetrahydronaphthalene- 2-acetate
(402) ethyl 7-[[4-[4-(2-pyridyl)piperadinoiminomethyl]benzoyl]amino]-1,2,3,4-tetrahydronaphthalene-2-acetate
(403) ethyl 7-[[4-(morpholinoiminomethyl)benzoyl]-N-methylamino]-1,2,3,4-tetrahydronaphthalene-2-acetate
(404) ethyl 6-[[4-(morpholinoiminomethyl)benzoyl]-N-methylamino]-1,2,3,4-tetrahydronaphthalene-2-acetate
(405) ethyl 7-[[4-(morpholinoiminomethyl)benzoyl]-N-n-butylamino]-1,2,3,4-tetrahydronaphthalene-2-acetate
(406) ethyl 6-[[4-(morpholinoiminomethyl)benzoyl]-N-methylamino]chroman-3-acetate
(407) ethyl 7-[[4-(morpholinoiminomethyl)benzoyl]-N-methylamino]chroman-3-acetate
(408) ethyl 7-[[4-(morpholinoiminomethyl)benzoyl]-N-methylamino]-1,2,3,4-tetrahydroisoquinoline-2-acetate
(409) ethyl 7-[[4-(thiomorpholinoiminomethyl)benzoyl]-N-methylamino]-1,2,3,4-tetrahydronaphthalene-2-acetate
(410) ethyl 6-[[4-(thiomorpholinoiminomethyl)benzoyl]-N-methylamino]-1,2,3,4-tetrahydronaphthalene-2-acetate
(411) ethyl 6-[[4-(thiomorpholinoiminomethyl)benzoyl]-N-methylamino]chroman-3-acetate
(412) ethyl 7-[[4-(thiomorpholinoiminomethyl)benzoyl]-N-methylamino]chroman-3-acetate
(413) ethyl 7-[[4-(thiomorpholinoiminomethyl)benzoyl]-N-methylamino]-1,2,3,4-tetrahydroisoquinoline-2-acetate
(414) ethyl 7-[[4-($N^2$-propargylamidino)benzoyl]-N-methylamino]-1,2,3,4-tetrahydroisoquinoline-2-acetate
(415) ethyl 7-[[4-($N^2$-propargylamidino)benzoyl]-N-n-butylamino]-1,2,3,4-tetrahydroisoquinoline-2-acetate
(416) ethyl 7-[N-[4-(morpholinoiminomethyl)phenyl]-N-methylcarbamoyl]-1,2,3,4-tetrahydronaphthalene-2-acetate (417) ethyl 6-[N-[4-(morpholinoiminomethyl)phenyl]-N-methylcarbamoyl]-1,2,3,4-tetrahydronaphthalene-2-acetate
(418) ethyl 6-[N-[4-(morpholinoiminomethyl)phenyl]-N-methylcarbamoyl]chroman-3-acetate
(419) ethyl 7-[N-[4-(morpholinoiminomethyl)phenyl]-N-methylcarbamoyl]chroman-3-acetate
(420) ethyl 7-[N-[4-(morpholinoiminomethyl)phenyl]-N-methylcarbamoyl]-1,2,3,4-tetrahydroisoquinoline-2-acetate
(421) ethyl 6-[N-[4-(morpholinoiminomethyl)phenyl]-N-methylcarbamoyl]-1,2,3,4-tetrahydroisoquinoline-2-acetate
(422) ethyl 7-[N-[4-(thiomorpholinoiminomethyl)phenyl]-N-methylcarbamoyl]-1,2,3,4-tetrahydronaphthalene-2-acetate
(423) ethyl 6-[N-[4-(thiomorpholinoiminomethyl)phenyl]-N-methylcarbamoyl]-chroman-3-acetate
(424) ethyl 7-[N-[4-(thiomorpholinoiminomethyl)phenyl]-N-methylcarbamoyl]-1,2,3,4-tetrahydroisoquinoline-2-acetate
(425) ethyl 7-[N-[4-($N^2$-propargylamidino)phenyl]-N-methylcarbamoyl]-1,2,3,4-tetrahydronaphthalene-2-acetate
(426) ethyl 6-[N-[4-($N^2$-propargylamidino)phenyl]-N-methylcarbamoyl]chroman-3-acetate
(427) ethyl 7-[N-[4-($N^2$-propargylamidino)phenyl]-N-methylcarbamoyl]-1,2,3,4-tetrahydroisoquinoline-2-acetate
(428) 7-[[4-[(1,1-dioxo)thiomorpholinoiminomethyl]benzoyl]amino]-1,2,3,4-tetrahydronaphthalene-2-acetic acid
(429) methyl 7-[[4-[(1,1-dioxo)thiomorpholinoiminomethyl]benzoyl]amino]-1,2,3,4-tetrahydronaphthalene-2-acetate
(430) ethyl 7-[[4-[(1,1-dioxo)thiomorpholinoiminomethyl]benzoyl]amino]- 1,2,3,4-tetrahydronaphthalene-2-acetate
(431) 6-[[4-[(1,1-dioxo)thiomorpholinoiminomethyl]benzoyl]amino]chroman-3-acetic acid
(432) ethyl 6-[[4-[(1,1-dioxo)thiomorpholinoiminomethyl]benzoyl]amino]chroman-3-acetate
(433) 7-[[4-[(1,1-dioxo)thiomorpholinoiminomethyl]benzoyl]amino]-1,2,3,4-tetrahydroisoquinoline-2-acetic acid
(434) ethyl 7-[[4-[(1,1-dioxo)thiomorpholinoiminomethyl]benzoyl]amino]-1,2,3,4-tetrahydroisoquinoline-2-acetate
(435) 7-[[4-[(1-oxo)thiomorpholinoiminomethyl]benzoyl]amino]-1,2,3,4-tetrahydronaphthalene-2-acetic acid
(436) ethyl 7-[[4-[(1-oxo)thiomorpholinoiminomethyl]benzoyl]amino]-1,2,3,4-tetrahydronaphthalene-2-acetate When an asymmetric carbon atom is present in the molecule of the compound represented by formula (1) in the invention, both R- and S-configurations of the optical isomers regarding the asymmetric carbon atom are included in the scope of the invention.

Further, salts of the compound represented by formula (1) in the invention can also be exemplified as specific compounds of the invention. Salts of the compound represented by formula (1) include, for example, hydrochloride, hydrobromide, sulfate, nitrate, phosphate and salts of other inorganic acids; acetate, tartrate, citrate, fumarate, maleate, toluenesulfonate, methanesulfonate and salts of other organic acid; and when Z is a hydrogen atom, salts of the compound include a sodium salt, potassium salt, calcium salt, aluminum salt and other metal salts; and a salt with ammonia, primary amine such as methylamine, secondary amine such as dimethylamine, tertiary amine such as triethylamine and other organic bases. All of these salts can be pharmaceutically acceptable.

Next, the process for preparing the substituted amidine derivative of the invention will be illustrated.

The compounds represented by formula (1) can be prepared, for example, by the following process.

(a) A condensation reaction of marketed p-cyanobenzoic acid or p-cyanobenzoyl chloride with a compound represented by formula (2) or (3):

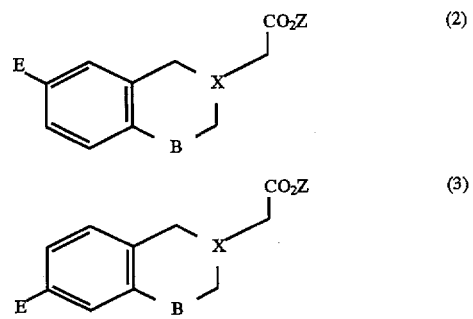

wherein E is —HN($R^1$) and B, X, Z and $R^1$ are the same as above, or (b) a condensation reaction of a compound represented by formula (4) or (5):

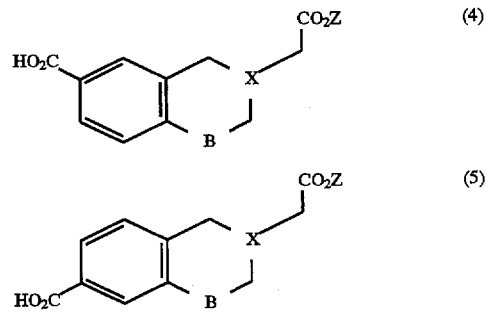

wherein B, X and Z are the same as above, or a compound represented by formula (6) or (7):

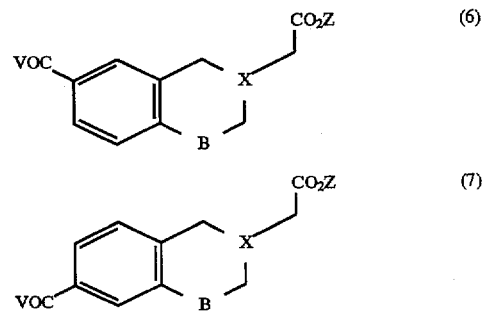

wherein V is a halogen atom and B, X and Z are the same as above, with a compound represented by formula (8):

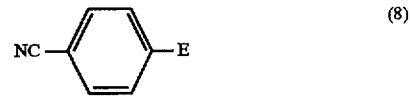

wherein E is the same as above, is carried out to obtain a compound represented by formula (9):

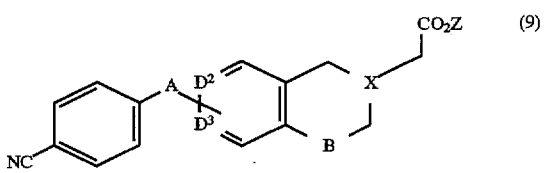

(9)

wherein A, B, X and Z are the same as above, $D^2$ and $D^3$ is a carbon atom and A is bonded to $D^2$ or $D^3$. The compound represented by formula (1) can be prepared by successively converting the cyano group of the above obtained compound of formula (9) to a substituted amidino group.

The compounds represented by formula (2) and (4) can be prepared from known compounds according to the process described in EP-A 0709370 and Example parts of this specification.

The compounds represented by formula (3) where X is

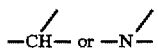

and B is —$CH_2$—, can be prepared from known compounds according to the process described in EP-A 0635492.

The compounds represented by formula (3) where X is

and B is —O—, can be prepared from 7-nitro-4-chromanone according to the process described in EP-A 0709370 and Example parts of this specification. 7-Nitro-4-chromanone can be prepared according to J. Med. Chem., 12, 277 (1969).

The compounds represented by formula (5) where X is

and B is —$CH_2$—, can be prepared from known compounds according to the process described in EP-A 0635492.

Further, the compounds represented by formula (5) where X is

and B is —$CH_2$— or X is

and B is —O—, can be prepared from 6-hydroxyisoquinoline or 7-hydroxy4-chromanone according to the process described in EP-A 0709370 or Example parts of this specification.

The condensation reaction of (a) and (b) can be carried out by the amide bond forming reaction of usual peptide, for example, the reaction using active ester, mixed anhydride or acid chloride. That is, in the condensation reaction of p-cyanobenzoic acid with the compounds of formula (2) or (3), or that of the compounds of formula (4) or (5) with the compounds of formula (8), p-cyanobenzoic acid or the compounds of formula (4) or (5) can be condensed with phenols such as 2,4,5-trichlorophenol, pentachlorophenol and 4-nitrophenol or N-hydroxy compounds such as N-hydroxysuccinimide, N-hydroxybenzotriazole and N-hydroxy-5-norbornene-endo-2,3-dicarboxyimide in the presence of dicyclohexylcarbodiimide to give the active ester. Thereafter, active ester thus obtained can be condensed with the compounds of formula (2) or (3), or the compounds of formula (8) to give the desired compound.

In another process, p-cyanobenzoic acid or the compounds of formula (4) or (5) is reacted with thionyl chloride, oxalyl chloride, phosphorus trichloride, phosphorus pentachloride or phosphorus oxychloride in the presence of a catalytic amount of N,N-dimethylformamide to give o-cyanobenzoyl chloride or the compounds of formula (6) or (7). p-Cyanobenzoyl chloride or the compounds of formula (6) or (7) thus obtained can be reacted with the compounds of formula (2) or (3), or the compounds of formula (8) to give the desired compounds.

In a further process, p-cyanobenzoic acid or the compound of formula (4) or (5) is reacted with isobutyl chloroformate to give a mixed anhydride. The mixed anhydride thus obtained can be successively condensed with the compounds of formula (2) or (3), or the compounds of formula (8) to give the desired compound. Further, the condensation reaction of p-cyanobenzoic acid with the compounds of formula (2) or (3), or said condensation reaction of the compounds of formula (4) or (5) with the compounds of formula (8) can also be carried out by single use of peptide condensation reagents such as dicyclohexyl-carbodiimide, N,N'-carbonyldiimidazole, diphenylphosphoryl azide or diethyl phosphorocyanidate.

The condensation reaction temperature is usually from −20° to 50° C., preferably from 0° C. to room temperature. Solvents which can be usually used include dioxane, N,N-dimethylformamide, dimethyl sulfoxide, chloroform, methylene chloride and tetrahydrofuran. Solvents are used singly or as a mixture.

The cyano group in the compound of formula (9) can be converted to the substituted amidino group by introducing hydrogen chloride gas in a solvent such as methanol or ethanol and successively reacting resultant imidate in methanol or ethanol with primary amine such as propargylamine and furfurylamine or secondary amine such as pyrrolidine, piperidine and morpholine. The reaction temperature is usually from −20° to 50° C., preferably from 0° C. to room temperature. Alternatively, conversion of the cyano group to the substituted amidino group can also be carried out by reacting with hydrogen sulfide and a base such as triethylamine in a solvent such as pyridine to obtain thioamide, treating thioamide in acetone with an alkylating agent such as methyl iodide and ethyl iodide to give an alkylthioimidoyl group, and treating the alkylthioimidoyl group with corresponding amine.

When Z in the compound of formula (1) contained in the final product is an alkyl group having 1–8 carbon atoms, 2-hydroxyethyl or 2-methoxyethyl, Z can be removed by known processes. For example, in the case of a compound having methyl ester or ethyl ester group, a carboxylic acid derivative can be obtained through hydrolysis of the ester group by treating with a base such as sodium hydroxide, potassium hydroxide and lithium hydroxide, or with an acid such as hydrochloric acid and acetic acid.

Salts of the compound represented by formula (1) can be obtained the reaction step for preparing the compound of formula (1). The salts of the compound represented by formula (1) can also be prepared by addition of acid or alkali, when necessary.

The thus obtained compound represented by formula (1) of the invention can be isolated from the reaction mixture by using common separation and purification methods such as extraction, concentration, neutralization, filtration, recrystallization and column chromatography.

The compounds and their salts which are represented by formula (1) in the invention are platelet aggregation inhibitors having GP IIb/IIIa antagonism, have excellent effect on oral administration as compared with compounds having an unsubstituted amidino group and thus are useful for prevention and treatment of acute and chronic diseases, in particular, caused by platelet thrombosis. Specifically, the compounds and their salts are useful for a preventive and remedy of peripheral circulatory impairments such as arteriosclerosis obliterans, thromboangiitis obliterans (Buerger disease), Raynaud disease, diabetic complication e.g. diabetic retinopathy and diabetic nephropathy, vein thrombosis e.g. deep vein thrombosis, ischemic cardiac disease such as angina pectoris e.g. stable angina pectoris and unstable angina pectoris including impending infarction, cardiac infarction e.g. acute myocardial infarction, and coronary thrombosis, ischemic brain disease such as cerebral infarction e.g. cerebral thrombosis and cerebral embolism, transient cerebral ischemic attack (TIA), and cerebrovascular contraction after bleeding, e.g. cerebrovascular twitch after subarachnoid hemorrhage, angiopulmonary impairment e.g. pulmonary thrombosis and pulmonary emboism, arterial thrombus and arterial sclerosis. Further, the compounds and their salts are useful for prevention of restenosis and reocclusion after percutaneous transluminal coronary angioplasty (PTCA) and percutaneous transluminal coronary recanalization (PTCR), prevention of reocclusion after administration of a tissue plasminogen activator (tPA), prevention of thrombocytopenia caused by dialysis, and prevention of thrombus formation due to artificial blood vessels and artificial organs. They are also useful for a preventive and remedy of disseminated intravascular coagulation syndrome (DIC) and inflammation e.g. nephritis, an inhibitor of cancer metastasis, and a preventive and remedy of immunological disease.

The compounds represented by formula (1) in the invention can be used in combination with an anti-platelet drug and anti-coagulation drug such as heparin, aspirin and warfarin.

The compounds and their salts represented by formula (1) in the invention exhibit no toxicity for ice even though an amount much exceeding the pharmaceutically active dose is administered.

When a medical composition containing the compound and its salt represented by formula (1) as an effective ingredient is used for a preventive of platelet aggregation, the dose and formulation naturally differ depending upon the properties of the compound and the symptom of a patient to be treated. In case of oral administration, 0.1–1000 mg/day, preferably 1–200 mg/day, for an adult can be administered in the formulation of tablet, granule, powder, suspension and capsule. In case of parenteral administration, 1–500 mg/day for an adult can be administered in the form of injection, suppository and isotonic liquid for infusion.

Formulation can be carried out according to known methods. For example, in case of preparing a tablet, corn starch, lactose, calcium phosphate and crystalline cellulose and the like are used as an excipient; hydroxypropyl cellulose, carboxymethyl cellulose and gum arabic and the like are used as a binder; starch, agar and calcium carbonate and the like are used as a disintegrator; and magnesium stearate and talc and the like are used as a lubricant. Sugar coating, gelatin coating and other suitable coatings can be applied to the tablet, when needed.

In case of preparing the injection, the compound of the invention can be used by dissolving in a physiological saline, alcohol, polyol, glycerol and vegetable oil.

No particular limitation is imposed upon the content of effective ingredients in a preparation. Both liquid and solid preparations usually have a content of 1–90%.

EXAMPLE

The present invention will hereinafter be illustrated in detail by the following examples. However, these examples are not to be construed to limit the scope of the invention. The number in parentheses after the name of an entitled compound is the number of the compound exemplified in the detailed description portion.

Reference Example 1

Synthesis of ethyl 7-[(4-amidinobenzoyl)amino]-1,2,3,4-tetrahydronaphthalene-2-acetate hydrochloride (1-1) A mixture of 7-nitro-1-tetralone (30 g) (manufactured by Lancaster Co.), 80% sulfuric acid (10 ml) and dioxane (60 ml) was heated to 90° C. and a 40% glyoxylic acid aqueous solution (30 ml) was added by three portions of 10 ml each at an interval of 1 hour and heated and refluxed for 3 hours. After allowing to cool the reaction mixture, the precipitated solid was filtered, washed with cold water and dried under reduced pressure to obtain 7-nitro-1-oxo-1,2,3,4-tetrahydro-2-naphthylideneacetic acid (33.3 g).

(1-2) In a 3000 ml autoclave, the compound (33.3 g) obtained in the step (1-1), ethanol (600 ml), concentrated sulfuric acid (24.0 ml) and 10% palladium/carbon (6.0 g) were mixed and stirred at 50° C. for 3 hours under hydrogen atmosphere at a pressure of 25 kg/cm$^2$ before reaction.

The catalyst was filtered off and the filtrate was concentrated under reduced pressure. Crude product thus obtained was purified by silica gel column chromatography to obtain ethyl 7-amino-1,2,3,4-tetrahydronaphthalene-2-acetate (18.3 g).

(1-3) 4-Cyanobenzoyl chloride (15.6 g) and the compound (18.3 g) obtained in the step (1-2) were suspended in chloroform (450 ml) and triethylamine (25.5 ml) was added under ice cooling. After stirring for 1 hour at room temperature, the chloroform layer was successively washed with a 1N hydrochloric acid solution, water, a saturated aqueous sodium bicarbonate solution and saturated aqueous sodium chloride solution, and dried with anhydrous magnesium sulfate. The solution was concentrated under reduced pressure and the crude product obtained was purified by silica gel column chromatography using a mixture, ethanol:chloroform=1:50, as a developer to obtain ethyl 7-[(4-cyanobenzoyl)amino]-1,2,3,4-tetrahydronaphthalene-2-acetate (12.6 g).

(1-4) To an ethanol solution (20 ml) of the compound (0.84 g) obtained in the step (1-3), hydrogen chloride gas was introduced for 30 minutes under ice cooling. The reaction mixture was allowed to stand overnight at room temperature. The solvent was distilled under reduced pressure and the crude product obtained was dissolved in ethanol (20 ml) and ammonium acetate (0.98 g) was added to the solution and the solution was stirred over night at room temperature. The solvent was distilled off under reduced pressure and the crude product obtained was recrystallized from ethanol to obtain the entitled compound (0.82 g).

mp: 207°–210° C.

$^1$HNMR(270 MHz,DMSO-d$_6$) δ ppm: 8.30(s,4H),8.08(d, 2H,J=8.8 Hz), 7.92(d,2H,J=8.8 Hz),7.50–7.48(m,2H),7.05 (d,1H,J=8.8 Hz),4.10(q,2H,J=7.3 Hz), 2.85–2.74(m,3H), 2.47–2.35(m,3H),2.14(brs,1H),1.91–1.87(m,1H), 1.49–1.34 (m,1H),1.21(t,3H,J=7.3 Hz)

Reference Example 2

Synthesis of 7-[(4-amidinobenzoyl)amino]-1,2,3,4-tetrahydronaphthalene-2-acetic acid hydrochloride The compound (0.1 g) obtained in Reference Example 1, the step (1-4) was suspended in ethanol (10 ml), a 2N aqueous sodium hydroxide solution (1.2 ml) was added and the mixture was stirred overnight at room temperature. After finishing the reaction, most of the solvent was distilled off under reduced pressure and the concentrated residue was acidified by adding a 3N aqueous hydrochloric acid solution. The formed precipitate was filtered, washed thoroughly with water to obtain the entitled compound (0.07 g).

mp: 236°–238° C.

$^1$HNMR(270 MHz,TFA-d) δ ppm:8.20(d,2H,J=8.8 Hz), 8.03(d,2H,J=8.8 Hz), 7.68–7.65(m,2H),7.34(d,1H,J=8.8 Hz),3.07–2.96(m,3H),2.69–2.59(m,3H), 2.41(brs,1H), 2.15–2.11(m,1H),1.71–1.56(m,1H)

APCI-MS: m/e=352(M$^+$+1)

Reference Example 3

Synthesis of ethyl 6-[(4-amidinobenzoyl)amino] chroman-3-acetate hydrochloride (3-1) Fuming nitric acid (200 ml) was cooled to from −30° to −35° C. and 4-chromanone (29.0 g) was added with stirring over 30 minutes. The mixture was further stirred for 30 minutes at the intact temperature and successively poured into ice water. The resulting mixture was extracted with ethyl acetate (2,500 ml). The organic layer was dried with anhydrous magnesium sulfate and the solvent was distilled off under reduced pressure to obtain the crude product as a yellow solid. The crude product was washed with a solvent mixture, n-hexane:ethyl acetate=1:1, to obtain 6-nitro-4-chromanone (27.0 g).

(3-2) The compound (27.0 g) obtained in the step (3-1) was subjected to the same reaction as carried out in Reference Example 1, the step (1-1) to obtain 6-nitro-4-oxo-3-chromanylideneacetic acid (20.0 g).

(3-3) The compound (18.7 g) obtained in the step (3-2) was subjected to the same reaction as carried out in Reference Example 1, the step (1-2) to obtain ethyl 6-aminochroman-3-acetate (13.0 g).

(3-4) The compound (13.0 g) obtained in the step (3-3) and 4-cyanobenzoyl chloride (11.0 g) were subjected to the same reaction as carried out in Reference Example 1, the step (1-3) to obtain ethyl 6-[(4-cyanobenzoyl)amino] chroman-3-acetate (8.9 g).

(3-5) The compound (0.89 g) obtained in the step (3-4) was subjected to the same reaction as carried out in Reference Example 1, step (1-4) to obtain the entitled compound (0.61 g, amorphous).

$^1$HNMR(270 MHz,DMSO-d$_6$) δ ppm:10.26(s,1H),8.29(s, 4H),8.10(d,2H,J=8.8 Hz), 7.92(d,2H,J=8.8 Hz),7.50(s,1H), 7.45(dd,1H,J=8.8,2.2 Hz),6.74(d,1H,J=8.8 Hz), 4.20–4.07 (m,3H),3.85–3.82(m,1H),2.92–2.86(m,1H),2.55–2.33(m, 4H), 1.21(t,3H,J=7.3 Hz)

Reference Example 4

Synthesis of 6-[(4-amidinobenzoyl)amino]chroman-3-acetic acid hydrochloride

The compound (0.34 g) obtained in Reference Example 3, the step (3-5) was subjected to the same reaction as carried out in Reference Example 2 to obtain the entitled compound (0.22 g, amorphous).

$^1$HNMR(270 MHz,DMSO-d$_6$) δ ppm:10.31(s,1H),9.50 (brs,2H),9.22(brs,2H), 8.14(d,2H,J=8.8 Hz),7.94(d,2H,J= 8.8 Hz),7.50(s,1H),7.45(dd,1H,J=8.8,2.2 Hz), 6.75(d,1H,J= 8.8 Hz),4.20–4.16(m,1H),3.85–3.78(m,1H),2.91–2.85(m, 1H), 2.57–2.51(m,4H)

Reference Example 5

Synthesis of ethyl 7-[(4-amidinobenzoyl)amino]-1,2,3,4-tetrahydroisoquinoline-2-acetate dihydrochloride (5-1) The raw material 7-nitro-1,2,3,4-tetrahydroisoquinoline was prepared according to Heterocyclic Chemistry, 22, 329 (1985).

7-Nitro-1,2,3,4-tetrahydroisoquinoline (5.78 g) was dissolved in ethanol (400 ml), triethylamine (7.8 ml) and ethyl bromoacetate (4.5 g) were added, and the mixture was heated and refluxed for 1 hour. Most of the solvent was distilled off under reduced pressure, concentrated residue was extracted with ethyl acetate and the extracted solution was dried with anhydrous magnesium sulfate. The solvent distilled off under reduced pressure and the crude product obtained was purified by silica gel column chromatography using a solvent mixture, ethyl acetate:n-hexane=1:3, as a developer. The compound obtained was treated with a hydrochloric acid/dioxane solution to obtain ethyl 7-nitro-1,2,3,4-tetrahydro-isoquinoline-2-acetate hydrochloride (4.2 g).

(5-2) The compound (4.2 g) obtained in the step (5-1) was suspended in ethanol (60 ml), 10% palladium/carbon (1.0 g) was added, and a catalytic hydrogenation reaction was carried out. Ethyl 7-amino-1,2,3,4-tetrahydroisoquinoline-2-acetate thus obtained was converted to dihydrochloride (4.4 g) by treating with a hydrochloric acid/dioxane solution. The dihydrochloride (4.4 g) was reacted with 4-cyanobenzoyl chloride (2.8 g) by the same procedures as carried out in Reference Example 1, the step (1-3). The reaction product thus obtained was treated with a hydrochloric acid/dioxane solution to obtain ethyl 7-[(4-cyanobenzoyl)amino]-1,2,3,4-tetrahydroisoquinoline-2-acetate hydrochloride (4.5 g).

(5-3) The compound (1.0 g) obtained in the step (5-2) was subjected to the same reaction as carried out in Reference Example 1, the step (1-4) to obtain the entitled compound (0.7 g).

mp: 172°–173° C.

$^1$HNMR(270 MHz,DMSO-d$_6$) δ ppm: 10.38(s,1H),8.30 (s,4H),8.14(d,2H,J=8.8 Hz), 7.94(d,2H,J=8.8 Hz),7.54(s, 1H),7.50(dd,1H,J=8.8,2.2 Hz),7.10(d,1H,J=8.8 Hz), 4.13(q, 2H,J=7.3 Hz),3.70(s,2H),3.42(s,2H),2.80(s,4H),1.22(t,3H, J=7.3 Hz)

Reference Example 6

Synthesis of 7-[(4-amidinobenzoyl)amino]-1,2,3,4-tetrahydroisoquinoline-2-acetic acid dihydrochloride The compound (0.1 g) obtained in Reference Example 5, the step (5-3) was subjected to the same reaction as carried out in Reference Example 2 to obtain the entitled compound (0.03 g).

mp: 238°–240° C.

$^1$HNMR(270 MHz,DMSO-d$_6$) δ ppm: 10.43(s,1H),9.49 (brs,2H),9.36(brs,2H), 8.16(d,2H,J=8.8 Hz),7.96(d,2H,J= 8.8 Hz),7.61(s,1H),7.55(dd,1H,J=8.8,2.2 Hz), 7.12(d,2H,J= 8.8 Hz),3.82(s,2H),3.37(s,2H),2.93–2.75(m,4H)

Reference Example 7

Synthesis of ethyl 7-[(4-amidinobenzoyl)amino] chroman-3-acetate hydrochloride (7-1) 7-Nitro-4-chromanone (10.8 g) was subjected to the same reaction as carried out in Reference Example 1, the step (1-1) to obtain 7-nitro-4-oxo-3-chromanylideneacetic acid (8.0 g).

(7-2) The compound (5.0 g) obtained in the step (7-1) was subjected to the same reaction as carried out in Reference Example 1, the step (1-2) to obtain ethyl 7-aminochroman-3-acetate (3.4 g).

(7-3) The compound (1.3 g) obtained in the step (7-2) and 4-cyanobenzoyl chloride (1.1 g) were subjected to the same reaction as carried out in Reference Example 1, the step (1-3) to obtain ethyl 7-[(4-cyanobenzoyl)amino]chroman-3-acetate (0.9 g).

(7-4) The compound (0.9 g) obtained in the step (7-3) was subjected to the same reaction as carried out in Reference Example 1, step (1-4) to obtain the entitled compound (0.7 g).

mp: above 250° C.

$^1$HNMR(270 MHz,DMSO-$d_6$) δ ppm: 10.39(s,1H),9.52 (brs,2H),9.24(brs,2H), 8.15(d,2H,J=8.1 Hz),7.96(d,2H,J= 8.8 Hz),7.32–7.25(m,2H),7.03(d,1H,J=8.8 Hz), 4.21–4.06 (m,3H),3.85–3.81(m,1H),2.89–2.83(m,1H),2.52–2.33(m, 4H), 1.21(t,3H,J=7.3 Hz)

Reference Example 8

Synthesis of 7-[(4-amidinobenzoyl)amino]chroman-3-acetic acid hydrochloride

The compound (0.5 g) obtained in Reference Example 7, the step (7-4) was subjected to the same reaction as carried out in Reference Example 2 to obtain the entitled compound (0.25 g).

mp: 253°–256° C.

$^1$HNMR(270 MHz,DMSO-$d_6$) δ ppm: 10.38(s,1H),9.52 (brs,2H),9.24(brs,2H), 8.14(d,2H,J=8.1 Hz),7.95(d,2H,J= 8.8 Hz),7.32–7.22(m,2H),7.03(d,1H,J=8.8 Hz), 4.20(d,1H, J=10.3 Hz),3.83–3.77(m,1H),2.87–2.82(m,1H),2.51–2.18 (m,4H)

Reference Example 9

Synthesis of ethyl 7-[[4-[$N^2$-(n-propyl)amidino] benzoyl]amino]-1,2,3,4-tetrahydronaphthalene-2-acetate hydrochloride The compound (0.5 g) obtained in Reference Example 1, the step (1-3) was suspended in ethanol (30 ml) and cooled with ice. Hydrogen chloride gas was introduced to the solution until saturation while maintaining the reaction temperature in 5°–15° C. The reaction mixture was stirred overnight at room temperature and ethanol was distilled off under reduced pressure. Crude product thus obtained was suspended in ethanol (20 ml), and n-propylamine (0.25 g) was added and stirred overnight at room temperature. The formed precipitate was filtrated, thoroughly washed with ethanol, and successively dissolved in a hydrochloric acid/ethanol solution. The solution was concentrated under reduced pressure. The concentrated crude product was recrystallized from ethanol to obtain the entitled compound (0.48 g).

mp: above 250° C.

$^1$HNMR(270 MHz,DMSO-$d_6$) δ ppm: 10.35(s,1H),9.92 (brs,1H),9.58(brs,1H), 9.19(brs,1H),8.16(d,2H,J=8.8 Hz), 7.87(d,2H,J=8.8 Hz),7.52–7.50(m,2H), 7.06(d,1H,J=8.8 Hz),4.10(q,2H,J=7.3 Hz),3.47–3.40(m,2H),2.86–2.75(m, 3H), 2.49–2.35(m,3H),2.24–2.13(m,1H),1.92–1.87(m,1H), 1.73–1.65(m,2H), 1.50–1.35(m,1H),1.21(t,3H,J=7.3 Hz), 0.90(t,3H,J=7.3 Hz)

Reference Example 10

Synthesis of ethyl 7-[[4-[$N^1$-(n-butoxycarbonyl) amidino]benzoyl]amino]-1,2,3,4-tetrahydronaphthalene-2-acetate The compound (0.5 g) obtained in Reference Example 1, the step (1-4) was suspended in tetrahydrofuran (10 ml) and cooled with ice. To the suspension, triethylamine (0.2 ml) and n-butyl chloroformate (0.19 ml) were successively added and stirred overnight at room temperature. The solvent was distilled off under reduced pressure. The crude product thus obtained was purified by silica gel column chromatography using the mixture, methanol:chloroform= 1:25, as a developer to obtain the entitled compound (0.44 g).

mp: 164°–165° C.

$^1$HNMR(270 MHz,CDCl$_3$) δ ppm: 9.63(brs,1H),8.00(s, 1H),7.90(d,2H,J=8.8 Hz), 7.84(d,2H,J=8.8 Hz),7.38(s,1H), 7.34(d,1H,J=8.1 Hz),7.07(d,1H,J=8.1 Hz), 4.15(m,4H), 2.92–2.79(m,3H),2.57–2.35(m,3H),2.26(m,1H),1.98(m, 1H), 1.72(m,2H),1.45(m,3H),1.27(m,3H),0.96(t,3H,J=7.3 Hz)

Example 1

Synthesis of ethyl 7-[[4-(morpholinoiminomethyl) benzoyl]amino]-1,2,3,4-tetrahydronaphthalene-2-acetate hydrochloride (Compound No. 3)

The compound (0.5 g) obtained in Reference Example 1, the step (1-3) was suspended in ethanol (20 ml) and cooled with ice. Hydrogen chloride gas was introduced to the suspension until saturation while maintaining the temperature in 5°–15° C. The mixture was stirred overnight at room temperature and the solvent was distilled off under reduced pressure. The concentrated product was dried under reduced pressure and successively suspended in ethanol (20 ml). Morpholine (0.36 g) was added to the solution and stirred overnight at room temperature. The solvent was distilled off under reduced pressure and the crude product obtained was purified by silica gel column chromatography using a mixture, ethanol:water:ethyl acetate=2:1:10, as a developer. The compound obtained was treated with a hydrochloric acid/dioxane solution to obtain the entitled compound (0.28 g, amorphous).

$^1$HNMR(270 MHz,DMSO-$d_6$) δ ppm: 10.36(s,1H),9.69 (brs,2H),8.18(d,2H,J=8.8 Hz), 7.77(d,2H,J=8.8 Hz), 7.51–7.50(m,2H),7.05(d,1H,J=8.8 Hz),4.10(q,2H,J=7.3 Hz), 3.79(brs,4H),3.32(brs,4H),2.85–2.75(m,3H),2.47–2.35 (m,3H),2.12–2.08(m,1H), 1.91–1.87(m,1H),1.49–1.34(m, 1H),1.21(t,3H,J=7.3 Hz)

Example 2

Synthesis of 7-[[4-(morpholinoiminomethyl) benzoyl]amino]-1,2,3,4-tetrahydronaphthalene-2-acetic acid hydrochloride (Compound No. 1)

The compound (0.15 g) obtained in Example 1 was suspended in ethanol (10 ml), a 1N aqueous sodium hydroxide solution (1.5 ml) was added, and the mixture was stirred overnight. The solvent was distilled off under reduced pressure, a 3N aqueous hydrochloric acid solution was added, and the formed precipitate was filtered, washed with water, and dried under reduced pressure to obtain the entitled compound (0.09 g).

mp: 166°–168° C.

$^1$HNMR(270 MHz,DMSO-$d_6$) δ ppm: 10.32(s,1H),9.66 (brs,2H),8.17(d,2H,J=8.8 Hz), 7.77(d,2H,J=8.8 Hz), 7.51–7.49(m,2H),7.05(d,1H,J=8.8 Hz),3.76(brs,4H), 3.57 (brs,4H),2.87–2.75(m,3H),2.46–2.27(m,3H),2.12–2.08(m, 1H), 1.93–1.89(m,1H),1.49–1.34(m,1H)

Example 3

Synthesis of methyl 6-[[4-(morpholinoiminomethyl) benzoyl]amino]chroman-3-acetate hydrochloride (Compound No, 23)

(3-1) The compound (1.3 g) obtained in Reference Example 3, the step (3-2) was subjected in methanol to the same reaction as carried out in Reference Example 3, the step (3-3) to obtain methyl 6-aminochroman-3-acetate (0.87 g).

(3-2) The compound (0.87 g) obtained in the step (3-1) and 4-cyanobenzoyl chloride (0.73 g) were subjected to the same reaction as carried out in Reference Example 1, the step (1-3) to obtain methyl 6-[(4-cyanobenzoyl)amino] chroman-3-acetate (1.0 g)

(3-3) The compound (1.0 g) obtained in the step (3-2) was subjected to the same reaction as carried out in Example 1, and successively reacted with morpholine (0.75 g). The compound obtained was treated with a hydrochloric acid/ dioxane solution to obtain the entitled compound (0.7 g).

mp: 254°–256° C.

$^1$HNMR(270 MHz,DMSO-$d_6$) δ ppm: 10.31(s,1H),9.67 (brs,2H),8.17(d,2H,J=8.8 Hz), 7.76(d,2H,J=8.1 Hz), 7.52–7.43(m,2H),6.75(d,1H,J=8.8 Hz),4.20–4.16(m,1H), 3.91–3.40(m,9H),3.42(s,3H),2.92–2.86(m,1H),2.58–2.36 (m,4H)

Example 4

Synthesis of ethyl 6-[[4-(morpholinoiminomethyl) benzoyl]amino]chroman-3-acetate hydrochloride (Compound No. 24)

The compound (1.5 g) obtained in Reference Example 3, the step (3-4) was subjected to the same reaction as carried out in Example 1, and successively reacted with morpholine (1.1 g). The compound obtained was treated with a hydrochloric acid/dioxane solution to obtain the entitled compound (0.7 g).

mp: 243°–245° C.

$^1$HNMR(270 MHz,DMSO-$d_6$) δ ppm: 10.34(s,1H),9.71 (brs,2H),8.18(d,2H,J=8.8 Hz), 7.76(d,2H,J=8.8 Hz), 7.53–7.35(m,2H),6.75(d,1H,J=8.8 Hz),4.20–4.07(m,3H), 3.80–3.30(m,9H),2.99–2.86(m,1H),2.57–2.25(m,4H),1.21 (t,3H,J=7.3 Hz)

Example 5

Synthesis of 6-[[4-(morpholinoiminomethyl) benzoyl]amino]chroman-3-acetic acid hydrochloride (Compound No. 22)

The compound (0.70 g) obtained in Example 4 was subjected to the same reaction as carried out in Example 2 to obtain the entitled compound (0.40 g).

mp: 236°–238° C.

$^1$HNMR(270 MHz,DMSO-$d_6$) δ ppm: 10.30(s,1H),9.72 (brs,2H),8.17(d,2H,J=8.1 Hz), 7.76(d,2H,J=8.1 Hz), 7.51–7.46(m,2H),6.75(d,1H,J=8.8 Hz),4.20–4.16(m,1H), 3.88–3.32(brs,9H),2.91–2.85(m,1H),2.57–2.22(m,4H)

Example 6

Synthesis of 2-methoxyethyl 6-[[4-(morpholinoiminomethyl)benzoyl]amino]chroman-3-acetate hydrochloride (Compound No. 26)

Thionyl chloride (0.4 ml) was dropwise added to methoxyethanol (5 ml) with ice cooling and stirred for 10 minutes at the intact temperature. To the resulting solution the compound (0.2 g) obtained in Example 5 was added and stirred overnight at room temperature. The solvent was distilled off under reduced pressure and the concentrated residue was washed with ethyl ether to obtain the entitled compound (0.12 g).

mp: 235°–237° C.

$^1$HNMR(270 MHz,DMSO-$d_6$) δ ppm: 10.29(s,1H),9.72 (brs,2H),8.16(d,2H,J=8.1 Hz), 7.75(d,2H,J=8.1 Hz), 7.77–7.42(m,2H),6.76(d,1H,J=8.8 Hz),4.20–4.17(m,1H), 3.85–3.75(m,5H),3.57–3.52(m,2H),3.29(s,4H),3.27(s,3H), 3.06–2.87(m,1H), 2.58–2.36(m,4H)

Example 7

Synthesis of n-butyl 6-[[4-(morpholinoiminomethyl) benzoyl]amino]chroman-3-acetate hydrochloride (Compound No. 28)

The compound (0.2 g) obtained in Example 5, was suspended in n-butanol. Concentrated sulfuric acid (0.1 ml) was dropwise added to the suspension and heated at 100° C. for an hour. The solvent was distilled off under reduced pressure and the concentrated residue was purified by reversed $C_{18}$ column chromatography using a mixture, water:acetonitrile:trifluoroacetic acid=30:70:0.1, as a developer. The desired fraction was concentrated under reduced pressure. The concentrated residue was treated with a hydrochloric acid/dioxane solution to obtain the entitled compound (0.16 g).

mp: 245°–247° C.

$^1$HNMR(270 MHz,DMSO-$d_6$) δ ppm: 10.29(s,1H),9.69 (brs,1H),9.51(brs,1H), 8.16(d,2H,J=8.1 Hz),7.77(d,2H,J= 8.1 Hz),7.51–7.43(m,2H),6.76(d,1H,J=8.8 Hz), 4.19–4.16 (m,1H),4.06(m,2H),3.84–3.33(m,9H),2.91–2.86(m,1H), 2.86–2.34(m,4H),1.62–1.52(m,2H),1.41–1.27(m,2H),0.90 (t,3H,J=7.3 Hz)

Example 8

Synthesis of ethyl 7-[[4-(morpholinoiminomethyl) benzoyl]amino]chroman-3-acetate hydrochloride (Compound No. 33)

The compound (0.5 g) obtained in Reference Example 7, the step (7-3) was subjected to the same reaction as carried out in Example 1, and successively reacted with morpholine (0.36). The compound obtained was treated with a hydrochloric acid/dioxane solution to obtain the entitled compound (0.3 g).

mp: 237°–240° C.

$^1$HNMR(270 MHz,DMSO-$d_6$) δ ppm: 10.38(s,1H),9.71 (brs,1H),9.50(brs,1H), 8.16(d,2H,J=8.1 Hz),7.77(d,2H,J= 8.1 Hz),7.31–7.25(m,2H),7.03(d,1H,J=8.8 Hz), 4.21–4.07 (m,3H),3.84–3.33(m,9H),2.98–2.82(m,1H),2.51–2.25(m, 4H), 1.21(t,3H,J=7.3 Hz)

Example 9

Synthesis of 7-[[4-(morpholinoiminomethyl)benzoyl]amino]chroman-3-acetic acid hydrochloride (Compound No. 31)

The compound (0.3 g) obtained in Example 8 was subjected to the same reaction as carried out in Example 2 to obtain the entitled compound (0.1 g).

mp: 110°–114° C.

$^1$HNMR(270 MHz,DMSO-$d_6$) δ ppm: 10.36(s,1H),9.71(brs,2H),8.16(d,2H,J=8.1 Hz), 7.76(d,2H,J=8.1 Hz), 7.31–7.23(m,2H),7.02(d,1H,J=8.8 Hz),4.19(d,1H,J=11.0 Hz), 3.90–3.10(m,9H);2.88–2.73(m,1H),2.50–2.21(m,4H)

Example 10

Synthesis of ethyl 7-[[4-(morpholinoiminomethyl)benzoyl]amino]-1,2,3,4-tetrahydroisoquinoline-2-acetate dihydrochloride (Compound No. 42)

The compound (1.0 g) obtained in Reference Example 5, the step (5-2) was subjected to the same reaction as carried out in Example 1 and successively reacted with morpholine (0.72 g). The compound thus obtained was treated with hydrochloric acid/ethanol solution to obtain the entitled compound (0.4 g, amorphous).

$^1$HNMR(270 MHz,DMSO-$d_6$) δ ppm: 10.75(s,1H),9.85(brs,1H),9.79(brs,1H), 8.24(d,2H,J=8.1 Hz),7.78(d,2H,J=8.1 Hz),7.72(m,2H),7.24(d,1H,J=8.1 Hz), 4.62–4.40(m,2H),4.36(m,2H),4.26(q,2H,J=7.3 Hz),4.02–3.74(m,4H),3.62(m,2H), 3.62–3.50(brs,2H),3.33(s,2H),3.30–2.98(m,2H),1.27(t,3H,J=7.3 Hz)

Example 11

Synthesis of 7-[[4-(morpholinoiminomethyl)benzoyl]amino]-1,2,3,4-tetrahydroisoquinoline-2-acetic acid dihydrochloride (Compound No. 40)

The compound (0.4 g) obtained in Example 10 was subjected to the same reaction as carried out in Example 2 to obtain the entitled compound (0.25 g, amorphous).

$^1$HNMR(270 MHz,DMSO-$d_6$) δ ppm: 10.72(s,1H),9.80(brs,1H),9.78(brs,1H), 8.23(d,2H,J=8.1 Hz),7.78(d,2H,J=8.1 Hz),7.73(m,2H),7.24(d,1H,J=8.1 Hz), 4.52(m,2H),4.28(s,2H),3.90(brs,2H),3.86(brs,2H),3.82–3.44(brs,6H),3.25–3.02(brs,2H)

Example 12

Synthesis of ethyl 7-[[4-(thiomorpholinoiminomethyl)benzoyl]amino]-1,2,3,4-tetrahydronaphthalene-2-acetate hydrochloride (Compound No. 81)

The compound (0.5 g) obtained in Reference Example 1, the step (1-3) was subjected to the same reaction as carried out in Example 1 and successively reacted with thiomorpholine (0.43 g). The compound thus obtained was treated with a hydrochloric acid/ethanol solution to obtain the entitled compound (0.41 g).

mp: 210°–213° C.

$^1$HNMR(270 MHz,DMSO-$d_6$) δ ppm: 10.39(s,1H),9.75(brs,1H),9.69(brs,1H), 8.17(d,2H,J=8.8 Hz),7.78(d,2H,J=8.8 Hz),7.51(m,2H),7.06(d,1H,J=8.8 Hz), 4.10(q,2H,J=7.3 Hz),4.08(m,2H),3.54(m,2H),2.98–2.67(m,7H),2.52–2.33(m,3H), 2.12(brs,1H),1.88(m,1H),1.51–1.33(m,1H),1.21(t,3H,J=7.3 Hz)

Example 13

Synthesis of 7-[[4-(thiomorpholinoiminomethyl)benzoyl]amino]-1,2,3,4-tetrahydronaphthalene-2-acetic acid hydrochloride (Compound No. 79)

The compound (0.15 g) obtained in Example 12 was subjected to the same reaction as carried out in Example 2 to obtain the entitled compound (0.08 g, amorphous).

$^1$HNMR(270 MHz,DMSO-$d_6$) δ ppm: 10.43(s,1H),9.75(brs,2H),8.19(d,2H,J=7.3 Hz), 7.77(d,2H,J=7.3 Hz),7.53(m,2H),7.05(d,1H,J=8.8 Hz),4.04–3.62(brs,4H), 2.97–2.60(brs,7H),2.50–2.23(m,3H),2.12(brs,1H),1.90(brs,1H), 1.50–1.31(m,1H)

Example 14

Synthesis of ethyl 7-[[4-(4-methylpiperazinoiminomethyl)benzoyl]amino]-1,2,3,4-tetrahydronaphthalene-2-acetate dihydrochloride (Compound No. 139)

The compound (0.5 g) obtained in Reference Example 1, the step (1-3) was subjected to the same reaction as carried out in Example 1 and successively reacted with N-methylpiperazine (0.41 g). The compound thus obtained was treated with a hydrochloric acid/ethanol solution to obtain the entitled compound (0.15 g)

mp: 234°–237° C.

$^1$HNMR(270 MHz,DMSO-$d_6$) δ ppm: 10.44(s,1H),10.18(brs,1H),10.03(brs,1H), 8.21(d,2H,J=8.8 Hz),7.81(d,2H,J=8.8 Hz),7.53(m,2H),7.06(d,1H,J=8.8 Hz), 4.10(q,2H,J=7.3 Hz),3.88–3.40(brs,8H),2.88–2.72(m,6H),2.52–2.35(m,3H), 2.12(brs,1H),1.89(m,1H),1.50–1.36(m,1H),1.21(t,3H,J=7.3 Hz)

Example 15

Synthesis of 7-[[4-(4-methylpiperazinoiminomethyl)benzoyl]amino]-1,2,3,4-tetrahydronaphthalene-2-acetic acid dihydrochloride (Compound No. 137)

The compound (0.15 g) obtained in Example 14 was subjected to the same reaction as carried out in Example 2 to obtain the entitled compound (0.05 g, amorphous).

$^1$HNMR(270 MHz,DMSO-$d_6$) δ ppm: 10.48(s,1H),10.18(brs,1H),10.03(brs,1H), 8.18(d,2H,J=8.1 Hz),7.70(d,2H,J=8.1 Hz),7.55(m,2H),7.04(d,1H,J=8.8 Hz), 3.57(brs,8H),2.98–2.65(m,6H),2.53–2.34(m,3H),2.13(m,1H),1.90(brs,1H), 1.52–1.33(brs,1H)

Example 16

Synthesis of ethyl 6-[[4-(4-methylpiperazinoiminomethyl)benzoyl]amino]chroman-3-acetate dihydrochloride (Compound No. 151)

The compound (1.05 g) obtained in Reference Example 3, the step (3-4) was subjected to the same reaction as carried out in Example 1 and successively reacted with N-methylpiperazine (1.2 g). The compound thus obtained was treated with a hydrochloric acid/dioxane solution to obtain the entitled compound (0.12 g).

mp: above 250° C.

$^1$HNMR(270 MHz,DMSO-$d_6$) δ ppm: 10.39(s,1H), 9.80–9.10(brs,3H), 8.16(d,2H,J=8.1 Hz),7.98(d,2H,J=8.1 Hz),7.52(d,1H,J=2.2 Hz), 7.48(dd,1H,J=8.8 Hz),6.76(d,1H,J=8.8 Hz),4.37(t,2H,J=7.0 Hz), 4.22–4.07(m,3H),3.85–2.34(m,15H),1.21(t,3H,J=7.0 Hz)

Example 17

Synthesis of ethyl 7-[[4-(piperidinoiminomethyl) benzoyl]amino]-1,2,3,4-tetrahydronaphthalene-2-acetate hydrochloride (Compound No. 196)

The compound (0.5 g) obtained in Reference Example 1, the step (1-3) was subjected to the same reaction as carried out in Example 1 and successively reacted with piperidine (0.35 g). The compound thus obtained was treated with a hydrochloric acid/dioxane solution to obtain the entitled compound (0.28 g, amorphous).

$^1$HNMR(270 MHz,DMSO-d$_6$) δ ppm: 10.35(s,1H),9.49 (brs,1H),9.32(brs,1H), 8.16(d,2H,J=8.8 Hz),7.74(d,2H,J= 8.8 Hz),7.50–7.49(m,2H),7.06(d,1H,J=8.8 Hz), 4.10(q,2H, J=7.3 Hz),3.77(brs,2H),3.34(brs,2H),2.85–2.75(m,3H), 2.44–2.35(m,3H),2.13–2.08(m,1H),1.91–1.87(m,1H), 1.76–1.59(m,6H), 1.49–1.34(m,1H),1.21(t,3H,J=7.3 Hz)

Example 18

Synthesis of 7-[[4-(piperidinoiminomethyl)benzoyl] amino]-1,2,3,4-tetrahydronaphthalene-2-acetic acid hydrochloride (Compound No. 194)

The compound (0.28 g) obtained in Example 17 was subjected to the same reaction as carried out in Example 2 to obtain the entitled compound (0.14 g).

mp: 188°–191° C.

$^1$HNMR(270 MHz,DMSO-d$_6$) δ ppm: 10.39(s,1H),9.51 (brs,1H),9.46(brs,1H), 8.17(d,2H,J=8.1 Hz),7.74(d,2H,J= 8.1 Hz),7.51(brs,2H),7.05(d,1H,J=8.8 Hz), 3.90–3.72(brs, 2H),3.35–3.20(brs,2H),2.90–2.69(m,3H),2.53–2.26(m,3H), 2.13(m,1H),1.90(brs,1H),1.77(brs,2H),1.65(brs,2H),1.55 (brs,2H), 1.52–1.33(m,1H)

Example 19

Synthesis of ethyl 6-[[4-(piperidinoiminomethyl) benzoyl]amino]chroman-3-acetate hydrochloride (Compound No. 209)

The compound (1.05 g) obtained in Reference Example 3, the step (3-4) was subjected to the same reaction as carried out in Example 1 and successively reacted with piperidine (0.7 g). The compound thus obtained was treated with a hydrochloric acid/dioxane solution to obtain the entitled compound (0.45 g).

mp: 200° C. (decomposition)

$^1$HNMR(270 MHz,DMSO-d$_6$) δ ppm: 10.32(s,1H),9.49 (brs,1H),9.37(brs,1H), 8.16(d,2H,J=8.1 Hz),7.74(d,2H,J= 8.1 Hz),7.52(d,1H,J=2.2 Hz), 7.46(dd,1H,J=2.2, 8.8 Hz), 6.76(d,1H,J=8.8 Hz),4.20–4.01(m,4H), 3.87–3.75(m,2H), 3.33–3.25(m,2H),2.93–2.84(m,1H),2.58–2.35(m,4H), 1.80–1.50(m,6H),1.21(t,3H,J=7.0 Hz)

Example 20

Synthesis of 6-[[4-(piperidinoiminomethyl)benzoyl] amino]chroman-3-acetic acid hydrochloride (Compound No. 207)

The compound (0.11 g) obtained in Example 19 was subjected to the same reaction as carried out in Example 2 to obtain the entitled compound (0.05 g).

mp: above 250° C.

$^1$HNMR(270 MHz,DMSO-d$_6$) δ ppm: 10.30(s,1H),9.47 (brs,1H),9.35(brs,1H), 8.15(d,2H,J=8.1 Hz),7.70(d,2H,J= 8.1 Hz),7.50(d,1H,J=2.2 Hz), 7.43(dd,1H,J=2.2, 8.8 Hz), 6.75(d,1H,J=8.8 Hz),4.12–4.00(m,2H), 3.86–3.73(m,2H), 3.31–3.21(m,2H),2.90–2.83(m,1H),2.55–2.33(m,4H), 1.79–1.48(m,6H)

Example 21

Synthesis of ethyl 7-[[4-(pyrrolidinoiminomethyl) benzoyl]amino]-1,2,3,4-tetrahydronaphthalene-2-acetate hydrochloride (Compound No. 250)

The compound (0.5 g) obtained in Reference Example 1, the step (1-3) was subjected to the same reaction as carried out in Example 1 and successively reacted with pyrrolidine (0.36 g). The compound thus obtained was successively treated with a hydrochloric acid/dioxane solution to obtain the entitled compound (0.28 g).

mp: 264° C.

$^1$HNMR(90 MHz,DMSO-d$_6$) δ ppm: 10.35(s,1H),9.18 (brs,2H),8.11(d,2H,J=8.8 Hz), 7.82(d,2H,J=8.8 Hz),7.49(m, 2H),7.19(d,1H,J=8.8 Hz),4.08(q,2H,J=7.3 Hz), 3.48(m,4H) ,2.85–2.75(m,3H),2.47–2.35(m,3H),2.12–2.08(m,3H), 1.91–1.87(m,3H),1.49–1.34(m,1H),1.21(t,3H,J=7.3 Hz)

Example 22

Synthesis of ethyl 7-[[4-(homopiperidinoiminomethyl)benzoyl]amino]-1,2,3, 4-tetrahydronaphthalene-2-acetate hydrochloride (Compound No. 254)

The compound (0.5 g) obtained in Reference Example 1, the step (1-3) was subjected to the same reaction as carried out in Example 1 and successively reacted with homopiperidine (0.41 g). The compound thus obtained was treated with a hydrochloric acid/ethanol solution to obtain the entitled compound (0.15 g).

mp: 197°–199° C.

$^1$HNMR(270 MHz,DMSO-d$_6$) δ ppm: 10.42(s,1H),9.50 (brs,1H),9.30(brs,1H), 8.18(d,2H,J=8.8 Hz),7.74(d,2H,J= 8.8 Hz),7.52(m,2H),7.06(d,1H,J=8.8 Hz), 4.10(q,2H,J=7.3 Hz),3.75(t,2H,J=5.1 Hz),3.38(brs,2H),2.88–2.71(m,3H), 2.48–2.33(m,3H),2.12(brs,1H),1.89(m,3H),1.70–1.51(m, 6H),1.50–1.33(m,1H), 1.21(t,3H,J=7.3 Hz)

Example 23

Synthesis of ethyl 7-[[4-(N$^1$-propargylamidino) benzoyl]amino]-1,2,3,4-tetrahydronaphthalene-2-acetate (Compound No. 257)

The compound (0.5 g) obtained in Reference Example 1, the step (1-3) was subjected to the same reaction as carried out in Example 1 and propargylamine (0.28 g) was added. The mixture was stirred overnight at room temperature and the solvent was distilled off under reduced pressure. The concentrated residue was purified by silica gel column chromatography using a mixture, chloroform:methanol= 10:1, as a developer to obtain the entitled compound (0.1 g).

mp: 132°–134° C.

$^1$HNMR(270 MHz,DMSO-d$_6$) δ ppm: 10.15(s,1H),7.97 (d,2H,J=8.8 Hz), 7.90(d,2H,J=8.8 Hz),7.50–7.48(m,2H), 7.04(d,1H,J=8.8 Hz),6.80(brs,2H), 4.10(q,2H,J=7.3 Hz), 3.93(d,2H),3.01(t,1H,J=2.2 Hz),2.85–2.75(m,3H), 2.45–2.36(m,3H),2.12(m,1H),1.86(m,1H),1.44(m,1H),1.21 (t,3H,J=7.3 Hz)

APCI-MS: m/e=418(M$^+$+1)

Example 24

Synthesis of ethyl 7-[[4-(N$^2$-propargylamidino) benzoyl]amino]-1,2,3,4-tetrahydronaphthalene-2-acetate (Compound No. 260)

The compound (0.5 g) obtained in Reference Example 1, the step (1-3) was subjected to the same reaction as carried out in Example 1 and propargylamine (0.28 g) was added. The mixture was stirred overnight at room temperature and the solvent was distilled off under reduced pressure. The concentrated residue was purified by silica gel column chromatography using a mixture, chloroform:methanol= 10:1 as a developer to obtain the entitled compound (0.081 g).

mp: 201°–204° C.

$^1$HNMR(270 MHz,DMSO-$d_6$) δ ppm: 10.37(s,1H),9.79 (brs,2H),8.13(d,2H,J=8.1 Hz), 7.90(d,2H,J=8.1 Hz), 7.50–7.48(m,2H),7.06(d,1H,J=8.8 Hz), 4.31(d,2H,J=2.2 Hz),4.10(q,2H,J=7.3 Hz),3.50(t,1H,J=2.2 Hz), 2.85–2.75(m,3H),2.45–2.36(m,3H),2.12(m,1H),1.86(m,1H),1.42(m,1H), 1.21(t,3H,J=7.3 Hz)

APCI-MS: m/e=418(M$^+$+1)

Example 25

Synthesis of 7-[[4-(N$^2$-propargylamidino)benzoyl] amino]-1,2,3,4-tetrahydronaphthalene-2-acetic acid hydrochloride (Compound No. 258)

The compound (0.081 g) obtained in Example 24 was subjected to the same reaction as carried out in Example 2 to obtain the entitled compound (0.069 g, amorphous).

$^1$HNMR(270 MHz,DMSO-$d_6$) δ ppm:10.45(brs,1H), 10.32(s,1H),9.92(brs,1H), 9.44(brs,1H),8.13(d,2H,J=8.8 Hz),7.89(d,2H, J=8.1 Hz),7.51–7.49(m,2H), 7.05(d,1H,J=8.8 Hz),4.28(d,2H,J=2.2 Hz),3.41(s,1H),2.86–2.75(m,3H), 2.46–2.27(m,3H),2.11(m,1H),1.89(m,1H),1.45–1.42(m,1H)

Example 26

Synthesis of ethyl 6-[[4-(N$^2$-propargylamidino) benzoyl]amino]chroman-3-acetate hydrochloride (Compound No. 272)

The compound (0.5 g) obtained in Reference Example 3, the step (3-4) was subjected to the same reaction as carried out in Example 1 and successively reacted with propargylamine (0.23 g). The compound thus obtained was treated with a hydrochloric acid/dioxane solution to obtain the entitled compound (0.37 g).

mp: 211°–212° C.

$^1$HNMR(270 MHz,DMSO-$d_6$) δ ppm: 10.45(brs,1H), 10.31(s,1H),9.92(brs,1H), 9.44(brs,1H),8.14(d,2H,J=8.8 Hz),7.87(d,2H,J=8.8 Hz),7.51–7.43(m,2H), 6.75(d,1H,J=8.8 Hz),4.35(d,2H,J=2.2 Hz),4.34–4.07(m,3H),3.85–3.79 (m,1H), 3.51(t,1H,J=2.2 Hz),2.93–2.86(m,1H),2.58–2.25 (m,4H),1.21(t,3H,J=7.3 Hz)

Example 27

Synthesis of 6-[[4-(N$^2$-propargylamidino)benzoyl] amino]chroman-3-acetic acid hydrochloride (Compound No. 271)

The compound (0.15 g) obtained in Example 26 was subjected to the same reaction as carried out in Example 2 to obtain the entitled compound (0.07 g).

mp: 173°–175° C.

$^1$HNMR(270 MHz,DMSO-$d_6$) δ ppm: 10.44(brs,1H), 10.31(s,1H),9.91(brs,1H), 9.42(brs,1H),8.15(d,2H,J=8.8 Hz),7.88(d,2H,J=8.8 Hz),7.49–7.43(m,2H), 6.76(d,1H,J=8.8 Hz),4.35(d,2H,J=2.2 Hz),4.20–4.16(m,1H),3.85–3.78 (m,1H), 3.52(t,1H,J=2.2 Hz),2.91–2.85(m,1H),2.57–2.26 (m,4H)

Example 28

Synthesis of ethyl 7-[[4-(N$^2$-propargylamidino) benzoyl]amino]-1,2,3,4-tetrahydroisoquinoline-2-acetate dihydrochloride (Compound No. 284)

The compound (0.8 g) obtained in Reference Example 5, step (5-2) was subjected to the same reaction as carried out in Example 1 and successively reacted with propargylamine (0.38 g). The compound thus obtained was treated with a hydrochloric acid/dioxane solution to obtain the entitled compound (0.38 g, amorphous).

$^1$HNMR(270 MHz,DMSO-$d_6$) δ ppm: 10.40(brs,1H), 10.32(s,1H),9.95(brs,1H), 9.46(brs,1H),8.18(d,2H,J=8.1 Hz),7.91(d,2H,J=8.1 Hz),7.83–7.79(m,2H), 7.17–7.12(m,1H),4.74(q,2H,J=7.3 Hz),4.37–4.34(m,2H),4.30–4.13(m,4H), 3.51(t,1H,J=2.2 Hz),3.46–3.33(brs,4H),1.21(t,3H,J=7.3 Hz)

Example 29

Synthesis of ethyl 7-[[4-[N$^2$-(2-furfuryl)amidino] benzoyl]amino]-1,2,3,4-tetrahydronaphthalene-2-acetate hydrochloride (Compound No. 303)

The compound (0.5 g) obtained in Reference Example 1, the step (1-3) was subjected to the same reaction as carried out in Example 1 and successively reacted with furfurylamine (0.4 g). The compound thus obtained was treated with a hydrochloric acid/dioxane solution to obtain the entitled compound (0.5 g, amorphous).

$^1$HNMR(270 MHz,DMSO-$d_6$) δ ppm: 10.43(t,1H, J=5.8 Hz),10.35(s,1H), 9.84(brs,1H),9.50(brs,1H),8.15(d,2H,J= 8.8 Hz),7.87(d,2H,J=8.1 Hz), 7.70(d,1H,J=2.2 Hz), 7.51–7.49(m,2H),7.04(d,1H,J=8.8 Hz),6.58(d,1H,J=2.9 Hz), 6.48(d,1H,J=2.9 Hz),4.74(d,2H,J=5.8 Hz),4.09(q,2H, J=7.3 Hz),2.89–2.75(m,3H), 2.49–2.35(m,3H),2.25–2.13 (m,1H),1.96–1.87(m,1H),1.49–1.35(m,1H), 1.21(t,3H,J=7.3 Hz)

Example 30

Synthesis of 7-[[4-[N$^2$-(2-furfuryl)amidino]benzoyl] amino]-1,2,3,4-tetrahydronaphthalene-2-acetic acid hydrochloride (Compound No. 301)

The compound (0.15 g) obtained in Example 29 was subjected to the same reaction as carried out in Example 2 to obtain the entitled compound (0.11 g, amorphous).

$^1$HNMR(270 MHz,DMSO-$d_6$) δ ppm: 10.43(brs,1H), 10.33(s,1H),9.80(brs,1H), 9.50(brs,1H),8.14(d,2H,J=8.8 Hz),7.88(d,2H,J=8.8 Hz),7.69(d,1H,J=2.2 Hz), 7.51–7.49 (m,2H),7.05(d,1H,J=8.8 Hz),6.57–6.46(m,2H),4.70(s,2H), 2.87–2.75(m,3H),2.52–2.27(m,3H),2.22–2.11(m,1H), 1.94–1.89(m,1H), 1.49–1.34(m,1H)

Example 31

Synthesis of ethyl 6-[[4-[N$^2$-(2-furfuryl)amidino] benzoyl]amino]chroman-3-acetate hydrochloride (Compound No. 316)

The compound (0.5 g) obtained in Reference Example 3, the step (3-4) was subjected to the same reaction as carried out in Example 1 and successively reacted with furfurylamine (0.4 g). The compound thus obtained was treated with a hydrochloric acid/dioxane solution to obtain the entitled compound (0.51 g).

mp: 217°–219° C.

$^1$HNMR(270 MHz,DMSO-$d_6$) δ ppm: 10.45(brs,1H), 10.32(s,1H),9.77(brs,2H), 9.51(brs,1H),8.14(d,2H,J=8.8 Hz),7.87(d,2H,J=8.8 Hz),7.72(s,1H), 7.50–7.44(m,2H),6.75 (d,1H,J=8.8 Hz),6.59–6.48(m,2H),4.75(s,2H), 4.20–4.07(m, 3H),3.85–3.78(m,1H),2.91–2.85(m,1H),2.57–2.26(m,4H), 1.21(t,3H,J=7.3 Hz)

Example 32

Synthesis of ethyl 7-[[4-[N$^2$-(2-furfuryl)amidino] benzoyl]amino]1,2,3,4-tetrahydroisoquinoline-2-acetate dihydrochloride (Compound No. 327)

The compound (1.0 g) obtained in Reference Example 5, the step (5-2) was subjected to the same reaction as carried out in Example 1 and successively reacted with furfurylamine (0.8 g). The compound thus obtained was treated with a hydrochloric acid/ethanol solution to obtain the entitled compound (0.58 g, amorphous).

$^1$HNMR(270 MHz,DMSO-$d_6$) δ ppm: 10.76(s,1H),10.56 (brs,1H),9.98(brs,1H), 9.71(brs,1H),8.20(d,2H,J=8.1 Hz), 7.93(d,2H,J=8.1 Hz),7.73(m,3H), 7.25(d,1H,J=8.1 Hz),6.62 (d,1H,J=2.9 Hz),6.49(dd,1H,J=2.9,2.2 Hz), 4.78(d,2H,J=5.9 Hz),4.60–4.41(brs,2H),4.35(m,2H),4.26(q,2H,J=7.3 Hz), 3.79–3.50(brs,2H),3.23–3.01(brs,2H),1.27(t,3H,J=7.3 Hz)

Example 33

Synthesis of 7-[[4-[$N^2$-(2-furfuryl)amidino]benzoyl] amino]-1,2,3,4-tetrahydroisoquinoline-2-acetic acid dihydrochloride (Compound No. 325)

The compound (0.3 g) obtained in Example 32 was subjected to the same reaction as carried out in Example 2 to obtain the entitled compound (0.22 g).

mp: 230°–233° C.

$^1$HNMR(270 MHz,DMSO-$d_6$) δ ppm: 10.74(s,1H),10.55 (s,1H),9.96(s,1H), 9.69(s,1H),8.21(d,2H,J=8.1 Hz),7.92(d, 2H,J=8.1 Hz),7.70(m,3H), 7.24(d,1H,J=8.1 Hz),6.62(d,1H, J=2.9 Hz),6.49(dd,1H,J=2.9,2.2 Hz), 4.79(d,2H,J=5.9 Hz), 4.50(brs,2H),4.26(s,2H),3.70–3.48(brs,2H), 3.23–3.00(brs, 2H)

Example 34

Synthesis of ethyl 7-[[4-($N^1$-methyl-$N^2$-propargylamidino)benzoyl]amino]-1,2,3,4-tetrahydronaphthalene-2-acetate hydrochloride (Compound No. 346)

The compound (0.5 g) obtained in Reference Example 1, the step (1-3) was subjected to the same reaction as carried out in Example 1 and successively reacted with N-methylpropargylamine (0.43 g). The compound thus obtained was treated with a hydrochloric acid/ethanol solution to obtain the entitled compound (0.15 g, amorphous).

$^1$HNMR(270 MHz,DMSO-$d_6$) δ ppm: 10.40(s,1H),9.87 (brs,1H),9.57(brs,1H), 8.19(d,2H,J=8.1 Hz),7.75(d,2H,J= 8.1 Hz),7.52(m,2H),7.06(d,1H,J=8.8 Hz), 4.30–4.12(brs, 2H),4.10(q,2H,J=7.3 Hz),3.67(s,1H),3.31(s,3H), 2.88–2.70 (m,3H),2.48–2.32(m,3H),2.13(brs,1H),1.88(m,1H), 1.51–1.33(m,1H), 1.21(t,3H,J=7.3 Hz)

Example 35

Synthesis of 7-[[4-($N^2$-methyl-$N^2$-propargylamidino)benzoyl]amino]-1,2,3,4-tetrahydronaphthalene-2-acetic acid hydrochloride (Compound No. 344)

The compound (0.15 g) obtained in Example 34 was subjected to the same reaction as carried out in Example 2 to obtain the entitled compound (0.145 g, amorphous).

$^1$HNMR(270 MHz,DMSO-$d_6$) δ ppm: 10.42(s,1H),9.87 (brs,1H),9.57(brs,1H), 8.15(d,2H,J=8.1 Hz),7.68(d,2H,J= 8.1 Hz),7.52(m,2H),7.06(d,1H,J=8.8 Hz), 4.20(s,2H),3.57 (s,1H),3.14(s,3H),2.91–2.67(m,3H),2.52–2.28(m,3H), 2.13 (brs,1H),1.90(brs,1H),1.51–1.33(m,1H)

Example 36

Synthesis of ethyl 7-[[4-[$N^2$-(2-thenyl)amidino] benzoyl]amino]-1,2,3,4-tetrahydronaphthalene-2-acetate hydrochloride (Compound No. 384)

The compound (0.5 g) obtained in Reference Example 1, the step (1-3) was subjected to the same reaction as carried out in Example 1 and successively reacted with 2-thienylmethylamine (0.47 g). The compound thus obtained was treated with a hydrochloric acid/ethanol solution to obtain the entitled compound (0.30 g).

mp: above 250° C.

$^1$HNMR(270 MHz,DMSO-$d_6$) δ ppm: 10.64(brs,1H), 10.38(s,1H),9.92(brs,1H), 9.70(brs,1H),8.16(d,2H,J=8.1 Hz),7.89(d,2H,J=8.1 Hz), 7.56(dd,1H,J=5.1,1.5 Hz),7.49(m, 2H),7.28(d,1H,J=2.2 Hz),7.07(m,2H), 4.93(s,2H),4.10(q, 2H,J=7.3 Hz),2.88–2.70(m,3H),2.48–2.32(m,3H), 2.11(brs, 1H),1.90(m,1H),1.51–1.33(brs,1H),1.21(t,3H,J=7.3 Hz)

Example 37

Synthesis of 7-[[4-[$N^2$-(2-thenyl)amidino]benzoyl] amino]-1,2,3,4-tetrahydronaphthalene-2-acetic acid hydrochloride (Compound No. 383)

The compound (0.15 g) obtained in Example 36 was subjected to the same reaction as carried out in Example 2 to obtain the entitled compound (0.10 g).

mp: above 250° C.

$^1$HNMR(270 MHz,DMSO-$d_6$) δ ppm: 10.65(s,1H),10.45 (s,1H),9.92(s,1H), 9.70(s,1H),8.17(d,2H,J=8.1 Hz),7.91(d, 2H,J=8.1 Hz),7.55(m,3H), 7.31(d,1H,J=2.9 Hz),7.06(m,2H) ,4.97(d,2H,J=5.1 Hz),2.88–2.65(m,3H), 2.52–2.23(m,3H), 2.11(brs,1H),1.90(m,1H),1.51–1.31(brs,1H)

Example 38

Synthesis of ethyl 7-[[4-[$N^2$-(2-picolyl)amidino] benzoyl]amino]-1,2,3,4-tetrahydronaphthalene-2-acetate dihydrochloride (Compound No. 388)

The compound (0.5 g) obtained in Reference Example 1, the step (1-3) was subjected to the same reaction as carried out in Example 1 and successively reacted with 2-picolylamine (0.32 g). The compound thus obtained was treated with a hydrochloric acid/dioxane solution to obtain the entitled compound (0.4 g).

mp: 237°–239° C.

$^1$HNMR(270 MHz,DMSO-$d_6$) δ ppm: 10.41(t,1H,J=5.8 Hz),10.33(s,1H),9.76(brs,1H), 9.43(brs,1H),8.63(d,1H,J= 5.1 Hz),8.18(d,2H,J=8.8 Hz),7.96(d,2H,J=8.8 Hz), 7.90–7.86(m,1H),7.55–7.49(m,3H),7.43–7.39(m,1H),7.05 (d,1H,J=8.8 Hz), 4.87(d,2H,J=5.8 Hz),4.10(q,2H,J=7.3 Hz), 2.85–2.76(m,3H),2.42–2.35(m,3H), 2.15(m,1H),1.89(m, 1H),1.47–1.43(m,1H),1.22(t,3H,J=7.3 Hz)

Example 39

Synthesis of 7-[[4-[$N^2$-(2-picolyl)amidino]benzoyl] amino]-1,2,3,4-tetrahydronaphthalene-2-acetic acid dihydrochloride (Compound No. 387)

The compound (0.13 g) obtained in Example 38 was subjected to the same reaction as carried out in Example 2 to obtain the entitled compound (0.09 g, amorphous).

$^1$HNMR(270 MHz,DMSO-$d_6$) δ ppm: 10.40(brs,1H), 10.28(s,1H),9.76(brs,1H), 9.43(brs,1H),8.57(d,1H,J=4.4 Hz),8.10(d,2H,J=8.8 Hz),7.97(d,2H,J=8.8 Hz) 7.86–7.80(m, 1H),7.57–7.49(m,3H),7.35–7.30(m,1H),7.05(d,1H,J=8.8 Hz), 4.70(s,2H),2.87–2.66(m,3H),2.46–2.27(m,3H), 2.09–2.07(m,1H), 1.93–1.85(m,1H),1.49–1.34(m,1H)

Example 40

Synthesis of ethyl 7-[[4-[$N^2$-(3-picolyl)amidino] benzoyl]amino]-1,2,3,4-tetrahydronaphthalene-2-acetate dihydrochloride (Compound No. 392)

The compound (0.8 g) obtained in Reference Example 1, the step (1-3) was subjected to the same reaction as carried out in Example 1 and successively reacted with 3-picolylamine (0.71 g). The compound thus obtained was treated with a hydrochloric acid/dioxane solution to obtain the entitled compound (0.37 g, amorphous).

$^1$HNMR(270 MHz,DMSO-d$_6$) δ ppm: 10.70(t,1H,J=5.8 Hz),10.40(s,1H),9.95(brs,1H), 9.83(brs,1H),9.05(s,1H), 8.84–8.81(m,1H),8.52(d,1H,J=8.1 Hz), 8.17(d,2H,J=8.1 Hz),8.00(d,2H,J=8.8 Hz),7.95–7.90(m,1H),7.53–7.50(m,2H), 7.05(d,1H,J=S.8 Hz),4.96(d,2H,J=5.87 Hz),4.13(q,2H, J=7.3 Hz), 2.85–2.75(m,3H),2.47–2.35(m,3H),2.17–2.13 (m,1H),1.91–1.87(m,1H), 1.50–1.33(m,1H),1.21(t,3H,J=7.3 Hz)

Example 41

Synthesis of ethyl 7-[[4-[N$^2$-(4-picolyl)amidino] benzoyl]amino]-1,2,3,4-tetrahydronaphthalene-2-acetate dihydrochloride (Compound No. 396)

The compound (0.5 g) obtained in Reference Example 1, the step (1-3) was subjected to the same reaction as carried out in Example 1 and successively reacted with 4-picolylamine (0.32 g). The compound thus obtained was treated with a hydrochloric acid/dioxane solution to obtain the entitled compound (0.4 g, amorphous).

$^1$HNMR(270 MHz,DMSO-d$_6$) δ ppm: 10.66(t,1H,J=5.1 Hz),10.45(s,1H),9.91(brs,1H), 9.50(brs,1H),8.67(d,2H,J=5.8 Hz),8.19(d,2H,J=8.8 Hz),8.01(d,2H,J=8.1Hz), 7.59(d, 2H,J=5.8 Hz),7.54–7.51(m,2H),7.04(d,1H,J=8.8 Hz),4.88 (d,2H,J=5.8 Hz), 4.09(q,2H,J=7.3 Hz),2.89–2.75(m,3H), 2.49–2.35(m,3H),2.25–2.13(m,1H), 1.96–1.87(m,1H), 1.49–1.35(m,1H),1.21(t,3H,J=7.3 Hz)

Example 42

Synthesis of ethyl 7-[[4-[N$^2$-[2-(4-pyridyl)ethyl] amidino]benzoyl]amino]-1,2,3,4-tetrahydronaphthalene-2-acetate dihydrochloride (Compound No. 400)

The compound (0.5 g) obtained in Reference Example 1, the step (1-3) was subjected to the same reaction as carried out in Example 1 and successively reacted with 4-(2-aminoethyl)pyridine (0.51 g). The compound thus obtained was treated with a hydrochloric acid/ethanol solution to obtain the entitled compound (0.098 g, amorphous).

$^1$HNMR(270 MHz,DMSO-d$_6$) δ ppm: 10.44(s,1H),10.23 (brs,1H),9.82(brs,1H), 9.73(brs,1H),8.88(d,2H,J=4.4 Hz), 8.16(d,2H,J=8.1 Hz),8.07(d,2H,J=5.9 Hz), 7.88(d,2H,J=8.1 Hz),7.53(m,2H),7.06(d,1H,J=8.8 Hz),4.10(q,2H,J=7.3 Hz), 3.92(d,2H,J=5.9 Hz),3.31(t,2H,J=7.3 Hz),2.91–2.68(m,3H), 2.48–2.32(m,1H), 2.14(brs,1H),1.89(m,1H),1.52–1.33(brs, 1H),1.21(t,3H,J=7.3 Hz)

Example 43

Synthesis of ethyl 7-[[4-(4-phenylpiperazinoiminomethyl)benzoyl]amino]-1,2,3, 4-tetrahydronaphthalene-2-acetate dihydrochloride (Compound No. 401)

The compound (0.8 g) obtained in Reference Example 1, the step (1-3) was subjected to the same reaction as carried out in Example 1 and successively reacted with N-phenylpiperazine (1.1 g). The compound thus obtained was treated with a hydrochloric acid/dioxane solution to obtain the entitled compound (0.9 g).

mp: 232°–235° C.

$^1$HNMR(270 MHz,DMSO-d$_6$) δ ppm: 10.39(s,1H),9.75 (brs,1H),9.72(brs,1H), 8.20(d,2H,J=8.1 Hz),7.81(d,2H,J=8.1 Hz),7.53–7.51(m,2H),7.30–7.24(m,2H), 7.07–7.01(m, 3H),6.90–6.84(m,1H),4.10(q,2H,J=7.3 Hz),4.04(brs,2H), 3.50(brs,4H),3.28(brs,2H),2.84–2.75(m,3H),2.49–2.35(m, 3H), 2.25–2.13(m,1H),1.92–1.87(m,1H),1.50–1.33(m,1H), 1.21(t,3H,J=7.3 Hz)

Example 44

Synthesis of ethyl 7-[[4-[4-(2-pyridyl) piperazinoiminomethyl]benzoyl]amino]-1,2,3,4-tetrahydronaphthalene-2-acetate trihydrochloride (Compound No. 402)

The compound (0.8 g) obtained in Reference Example 1, the step (1-3) was subjected to the same reaction as carried out in Example 1 and successively reacted with 4-(2-pyridyl)piperazine (1.1 g). The compound thus obtained was treated with a hydrochloric acid/dioxane solution to obtain the entitled compound (0.7 g, amorphous).

$^1$HNMR(270 MHz,DMSO-d$_6$) δ ppm: 10.41(s,1H),9.83 (brs,1H),9.73(brs,1H), 8.21(d,2H,J=8.1 Hz),8.08(dd,1H,J=5.8,1.4 Hz),7.99–7.93(m,1H), 7.81(d,2H,J=8.1 Hz), 7.53–7.51(m,2H),7.28(d,1H,J=8.8 Hz),7.07–7.03(m,1H), 6.98–6.93(m,1H),4.17–4.06(m,4H),3.84(brs,2H),3.61(brs, 2H), 2.86–2.75(m,3H),2.47–2.35(m,3H),2.17–2.13(m,1H), 1.92–1.88(m,1H), 1.50–1.40(m,1H),1.21(t,3H,J=7.3 Hz)

[Synthesis of optically active compounds]

Reference Example 11

Synthesis of methyl (–)-7-amino-1,2,3,4-tetrahydronaphthalene-2-acetate

The racemate of methyl 7-amino-1,2,3,4-tetrahydronaphthalene-2-acetate hydrochloride (7.0 g) which was obtained by carrying out the reaction of Reference Example 1, the step (1-2) in methanol, was resolved and fractionated by high performance liquid chromatography to obtain the (–)-isomer (2.5 g) having optical purity of 97% and the (+)-isomer (2.5 g) having optical purity of 96%.

(–)-isomer
  mp: 49°–51° C.
  $[\alpha]_D^{25}$=–69.0 (C=1.00, MeOH)
(+)-isomer
  mp: 49°–51° C.
  $[\alpha]_D^{25}$=+68.3 (C=1.00, MeOH)

Fractionating was carried out under the following conditions.

High performance liquid chromatograph: LC-10A
(Manufactured by Shimadzu Seisakusho Co.)
Column: chiral cell OD 20 mm×250 mm
(Manufactured by Daicel Chemical Co.)
Wave length: 254 nm
Flow rate: 16 ml/min
Moving phase: n-hexane/ethanol=10/1

Reference Example 12

Synthesis of (–)-methyl 6-aminochroman-3-acetate

The racemate of methyl 6-aminochroman-3-acetate (9.15 g) which was obtained by carrying out the same reaction in methanol as described in Reference Example 3, the step (3-3), was resolved and fractionated by high performance liquid chromatography to obtain the (–)-isomer (4.29 g) having optical purity of 99% and the (+)-isomer (4.29 g) having optical purity of 99%.

(−)-isomer
mp: 104°–106° C.
$[\alpha]_D^{25}$=−28.4 (C=0.43, MeOH)
(+)-isomer
mp: 49°–51° C.
$[\alpha]_D^{25}$=+28.4 (C=0.43, MeOH)

Fractionation was carried out under the following conditions.

High performance liquid chromatograph: LC-10A
(Manufactured by Shimadzu Seisakusho Co.)
Column: chiral cell OD 20 mm×250 mm
(Manufactured by Daicel Chemical Co.)
Wave length: 254 nm
Flow rate: 16 ml/min
Moving phase: n-hexane/ethanol=5/1

Example 45

Synthesis of ethyl (−)-7-[[4-($N^2$-propargylamidino)benzoyl]amino]-1,2,3,4-tetrahydronaphthalene-2-acetate hydrochloride The (−)-isomer (0.5 g) obtained in Reference Example 11 was subjected to the same reaction as carried out in Reference Example 1, the step (1-3) and Example 24, and successively reacted with propargylamine (0.28 g). The resulting compound was treated with a hydrochloric acid/dioxane solution to obtain the entitled compound (0.45 g).

mp: 235°–237° C.

$^1$HNMR(270 MHz,DMSO-$d_6$) δ ppm: 10.42(brs,1H), 10.37(s,1H),9.79(brs,2H), 8.13(d,2H,J=8.1 Hz),7.90(d,2H,J=8.1 Hz),7.51–7.48(m,2H),7.06(d,1H,J=8.8 Hz), 4.31(d,2H,J=2.2 Hz),4.10(q,2H,J=7.3 Hz),3.50(t,1H,J=2.2 Hz), 2.85–2.75(m,3H), 2.45–2.36(m,3H),2.12(m,1H),1.86(m,1H),1.44(m,1H),1.21(t,3H,J=7.3 Hz)

$[\alpha]_D^{25}$=−60.8 (C=0.15, EtOH)

Example 46

Synthesis of (−)-7-[[4-($N^2$-propargylamidino)benzoyl]amino]-1,2,3,4-tetrahydronaphthalene-2-acetic acid hydrochloride The compound (0.30 g) obtained in Example 45 was subjected to the same reaction as carried out in Example 2 to obtain the entitled compound (0.15 g).

mp: 235°–236° C.

$^1$HNMR(270 MHz,DMSO-$d_6$) δ ppm: 10.45(brs,1H), 10.32(s,1H),9.92(brs,1H), 9.44(brs,1H),8.13(d,2H,J=8.1 Hz),7.90(d,2H,J=8.1 Hz),7.51–7.49(m,2H), 7.05(d,1H,J=8.8 Hz),4.28(d,2H,J=2.2 Hz),3.41(t,1H,J=2.2 Hz),2.86–2.75 (m,3H), 2.46–2.27(m,3H),2.11(m,1H),1.89(m,1H),1.45–1.42(m,1H)

$[\alpha]_D^{25}$=−49.5 (C=0.12, EtOH)

Example 47

Synthesis of ethyl (−)-7-[[4-(morpholinoiminomethyl)benzoyl]amino]-1,2,3,4-tetrahydronaphthalene-2-acetate hydrochloride The (−)-isomer (0.5 g) obtained in Reference Example 11 was subjected to the same reaction as carried out in Reference Example 1, the step (1-3) and Example 1, and successively reacted with morpholine (0.36 g). The compound thus obtained was treated with a hydrochloric acid/dioxane solution to obtain the entitled compound (0.25 g).

mp: 238°–240° C.

$^1$HNMR(270 MHz,DMSO-$d_6$) δ ppm: 10.36(s,1H),9.69(brs,2H),8.18(d,2H,J=8.8 Hz), 7.77(d,2H,J=8.8 Hz),7.51–7.49(m,2H),7.05(d,1H,J=8.8 Hz), 4.10(q,2H,J=7.3 Hz),3.79(brs,4H),3.32(brs,4H),2.85–2.75(m,3H), 2.47–2.35(m,3H),2.12–2.08(m,1H),1.91–1.87(m,1H),1.49–1.34(m,1H), 1.21(t,3H,J=7.3 Hz)

$[\alpha]_D^{25}$=−55.0 (C=0.15, MeOH)

Example 48

Synthesis of (−)-7-[[4-(morpholinoiminomethyl)benzoyl]amino]-1,2,3,4-tetrahydronaphthalene-2-acetic acid hydrochloride The compound (0.2 g) obtained in Example 47 was subjected to the same reaction as carried out in Example 2 to obtain the entitled compound (0.11 g).

mp: 235°–237° C.

$^1$HNMR(270 MHz,DMSO-$d_6$) δ ppm: 10.32(s,1H),9.66(brs,2H),8.17(d,2H,J=8.8 Hz), 7.77(d,2H,J=8.8 Hz),7.51–7.49(m,2H),7.05(d,1H,J=8.8 Hz),3.76(brs,4H), 3.57(brs,4H),2.87–2.75(m,3H),2.46–2.27(m,3H),2.12–2.08(m,1H), 1.93–1.89(m,1H),1.49–1.34(m,1H)

$[\alpha]_D^{25}$=−60.0 (C=0.03, EtOH)

Example 49

Synthesis of ethyl (−)-6-[[4-($N^2$-propargylamidino)benzoyl]amino]chroman-3-acetate hydrochloride The (−)-isomer (0.5 g) obtained in Reference Example 12 was subjected to the same reaction as carried out in Reference Example 3, the step (3-4) and Example 26 and successively reacted with propargylamine (0.23 g). The compound thus obtained was treated with a hydrochloric acid/dioxane solution to obtain the entitled compound (0.45 g).

mp: 234°–236° C.

$^1$HNMR(270 MHz,DMSO-$d_6$) δ ppm: 10.45(brs,1H), 10.31(s,1H),9.92(brs,1H), 9.44(brs,1H),8.14(d,2H,J=8.8 Hz),7.87(d,2H,J=8.8 Hz),7.51–7.43(m,2H), 6.75(d,1H,J=8.8 Hz),4.35(d,2H,J=2.2 Hz),4.34–4.07(m,3H),3.85–3.79(m,1H), 3.51(t,1H,J=2.2 Hz),2.93–2.86(m,1H),2.58–2.25(m,4H),1.21(t,3H,J=7.3 Hz)

Example 50

Synthesis of (−)-6-[[4-($N^2$-propargylamidino)benzoyl]amino]chroman-3-acetic acid hydrochloride The compound (0.3 g) obtained in Example 49 was subjected to the same reaction as carried out in Example 2 to obtain the entitled compound (0.15 g).

mp: 240°–242° C.

$^1$HNMR(270 MHz,DMSO-$d_6$) δ ppm: 10.44(brs,1H), 10.31(s,1H),9.91(brs,1H), 9.42(brs,1H),8.15(d,2H,J=8.8 Hz),7.88(d,2H,J=8.8 Hz),7.49–7.43(m,2H), 6.76(d,1H,J=8.8 Hz),4.35(d,2H,J=2.2 Hz),4.20–4.16(m,1H),3.85–3.78(m,1H), 3.52(t,1H,J=2.2 Hz),2.91–2.85(m,1H),2.57–2.26(m,4H)

$[\alpha]_D^{25}$=−17.6 (C=0.47, MeOH)

Example 51

Synthesis of ethyl (−)-6-[[4-(morpholinoiminomethyl)benzoyl]amino]chroman-3-acetate hydrochloride The (−)-isomer (0.5 g) obtained in Reference Example 12 was subjected to the same reaction as carried out in Reference Example 3, the step (3-4) and Example 4 and successively reacted with morpholine (0.36 g). The compound thus obtained was treated with a hydrochloric acid/dioxane solution to obtain the entitled compound (0.45 g).

mp: 243°–245° C.

$^1$HNMR(270 MHz,DMSO-$d_6$) δ ppm: 10.34(s,1H),9.71 (brs,2H),8.18(d,2H,J=8.8 Hz), 7.76(d,2H,J=8.8 Hz), 7.53–7.45(m,2H),6.75(d,1H,J=8.8 Hz),4.20–4.07(m,3H), 3.80–3.30(m,9H),2.99–2.86(m,1H),2.57–2.25(m,4H),1.21 (t,3H,J=7.3 Hz)

$[\alpha]_D^{23}$=–16.0 (C=1.00, MeOH)

Example 52

Synthesis of (–)-6-[[4-(morpholinoiminomethyl) benzoyl]amino]chroman-3-acetic acid hydrochloride The compound (0.3 g) obtained in Example 51 was subjected to the same reaction as carried out in Example 2 to obtain the entitled compound (0.15 g).

mp: 234° C.

$^1$HNMR(270 MHz,DMSO-$d_6$) δ ppm: 10.30(s,1H),9.72 (brs,2H),8.17(d,2H,J=8.1 Hz), 7.76(d,2H,J=8.1 Hz), 7.51–7.46(m,2H),6.75(d,1H,J=8.8 Hz),4.20–4.16(m,1H), 3.88–3.32(m,9H),2.91–2.86(m,1H),2.57–2.22(m,4H)

$[\alpha]_D^{23}$=–13.7 (C=0.48, MeOH)

Pharmacological Test Example 1

Experiment for binding inhibition between GP IIb/IIIa and fibrinogen

1. Purification of human fibrinogen receptor GP IIb/IIIa

Concentrated and lyophilized human platelet (20 vial) (Organon Teknika Co.) was lysed in an antienzymic solution (80 ml) (1% Triton X-100, 10 mM Tris-HCl, 150 mM NaCl, 1 mM CaCl$_2$, 10 µM leupeptin, 1 mM phenylmethane sulfonyl fluoride, pH 7.4), allowed to incubate for an hour at 4° C., and centrifuged at 30,000×g for 15 minutes to recover the supernatant solution containing 150 mg of protein. The GP IIb/IIIa was purified according to the method of Phillips et al. [Methods in Enzymology Vol. 215, (J. J. Hawigar, Eds.), 244–263, Acedemic Press Inc., San Diego].

2. Preparation of biotinylated fibrinogen

Human fibrinogen Grade L (KABI Co.) was purified by using Shepharose CL-6B and Lysine-Sepharose. Thus purified human fibrinogen (2.3 mg/ml) was dialyzed for 3 hours with 0.1M aqueous sodium bicarbonate solution at room temperature and successively diluted to 1 mg/ml. To the solution (4.5 ml) obtained, NHC-LC-Biotin (2 mg) (Pierce Co.) was added and reacted for 1 hour at room temperature to biotinylate fibrinogen. The reaction mixture was dialyzed at 4° C. for 24 hours with TBS (20 mM Tris-HCl, 150 mM NaCl, 1 mM CaCl$_2$, 1 mM MgCl$_2$, pH 7.4) to obtain biotinylated fibrinogen.

3. Binding inhibition of biotinylated fibrinogen to GP IIb/IIIa

Specimen drugs were dissolved and diluted with TBS containing 1% BSA. To each solution, an equal volume of biotinylated fibrinogen (2 µg/ml) dissolved in TBS containing 1% BSA, was added. The inhibition percentage of specimen drugs were measured by the method of Mori et al. [Jpn. J. Thromb. Hemost., 2, 323–399 (1991) with small modification].

Purified GP IIb/IIIa was diluted to 1.5 µg/ml in TBS containing 0.0005% of Triton X-100. The GP IIb/IIIa solution was added to a 96 well microplate (E.I.A/R.I.A. Plate, Costar Co.) in a volume of 100 µl for each well, and incubated at 4° C. for 24 hours to immobilize GP IIb/IIIa. The microplate was washed twice with a washing solution (TBS containing 0.01% of Tween 20). Thereafter TBS containing 3.5% of BSA was added to each well in a volume of 200 µl and blocking was carried out for about an hour at room temperature. The microplate was further washed twice with the washing solution, and successively a mixture of the specimen drug and the biotinylated fibrinogen was added in a volume of 100 µl/well and incubated for 24 hours at room temperature. The microplate was thereafter washed five times, and peroxidase-labeled streptoavidin (a kit of Amersham Co.) which was previously diluted 3000 times with TBS was added in a volume of 100 µl/well and incubated for about 30 minutes at room temperature. After washing the microplate 5 times, a 0.05M phosphate-citrate buffer solution (pH$_5$) containing o-phenylenediamine (0.4 mg/ml) (manufactured by Sigma Co.) and H$_2$O$_2$ (0.012%) was added in a volume of 200 µl/well to develop color for 20–40 minutes. The reaction was stopped by addition of 0.3M sulfuric acid in a volume of 50 µl/well and absorbance at 490 nm was measured with Immunoreader NJ-200 (manufactured by Inter Med Co.). It was defined as the basis of inhibition percentage that the absorbance in the absence of the specimen drug was 0% inhibition and the absorbance in the case of adding 200 µM RGDS in place of the specimen drug was 100% inhibition. The concentration of the specimen drug giving 50% of binding inhibition was defined as IC$_{50}$. Results are illustrated in Table 1.

TABLE 1

| Inhibition of GPIIb/IIIa . Fibrinogen Binding | |
|---|---|
| Compound | IC$_{50}$(nM) |
| Compound of Example 2 | 0.13 |
| Compound of Example 13 | 0.28 |
| Compound of Example 18 | 0.26 |
| Compound of Example 25 | 0.18 |
| Compound of Example 30 | 0.14 |
| Compound of Example 37 | 0.04 |
| Compound of Example 46 | 0.11 |
| Compound of Example 48 | 0.07 |
| Compound of Example 50 | 0.22 |
| Compound of Example 52 | 0.13 |

It can be seen from the above results that the compounds of the invention can inhibit the binding between GP IIb/IIIa and fibrinogen as GP IIb/IIIa antagonists at very low concentrations.

Pharmacological Test Example 2

In vitro experiment of platelet aggregation inhibition
1. Inhibition of platelet aggregation in Guinea pig Blood of male guinea pig was collected with an injection syringe which contains 3.8 % sodium citrate as an anticoagulant in a ratio of 1 volume to 9 volumes of the blood. Successively, the collected blood mixture was subjected to centrifugation at 120×g for 15 minutes at room temperature to obtain platelet-rich plasma (PRP). An aliquot of PRP was further subjected to centrifugation at 1,200×g for 15 minutes to obtain platelet-poor plasma (PPP). Numbers of the platelet in PRP were measured with an automatic platelet counter: Sysmex PL-100 (manufactured by Toa Iyodenshi Co.) and PRP was diluted with PPP so as to adjust a platelet concentration to be about 300,000 particles/ µl. Platelet aggregation was measured by the following procedure with a 6 channel aggregometer: HEMA TRACER 1 (manufactured by NKK Co.).

After incubation of 240 µl of PRP at 37° C. for 2 minutes, 30 µl of the solvent of specimen as a control or of the specimen in various concentrations was added to PRP. Further 2 minutes later, 30 µl of adenosine diphosphate (final concentration: 5µM) was added to induce platelet aggregation. An inhibition percentage was obtained by comparing the maximum aggregation of the specimen drug group with that of control. A specimen drug concentration giving 50 % inhibition ($IC_{50}$) was calculated from the inhibition percentage and the specimen drug concentration, and used as an index of antiplatelet activity. Results are illustrated in Table 2.

TABLE 2

Platelet aggregation inhibitory activity in guinea pig

| Compound | $IC_{50}$(nM) |
| --- | --- |
| Compound of Example 1 | 180 |
| Compound of Example 2 | 140 |
| Compound of Example 4 | 120 |
| Compound of Example 13 | 170 |
| Compound of Example 14 | 66 |
| Compound of Example 17 | 270 |
| Compound of Example 21 | 94 |
| Compound of Example 22 | 250 |
| Compound of Example 25 | 280 |
| Compound of Example 26 | 190 |
| Compound of Example 30 | 180 |
| Compound of Example 31 | 140 |
| Compound of Example 37 | 220 |
| Compound of Example 39 | 140 |
| Compound of Example 40 | 110 |
| Compound of Example 41 | 120 |
| Compound of Example 42 | 130 |
| Compound of Example 43 | 140 |
| Compound of Example 44 | 88 |
| Compound of Example 46 | 150 |
| Compound of Example 48 | 69 |
| Compound of Example 50 | 200 |
| Compound of Example 52 | 110 |
| Compound of Ref. Example 2 | 370 |
| Compound of Ref. Example 4 | 480 |
| Compound of Ref. Example 6 | 6600 |
| Compound of Ref. Example 9 | 520 |

2. Inhibition of platelet aggregation in human

Blood was collected from healthy human volunteers with an injection syringe and mixed one volume of 3.8% of sodium citrate as an anticoagulant to 9 volumes of the blood. Successively, the obtained blood mixture was subjected to centrifugation at 120×g for 15 minutes at room temperature to obtain platelet-rich plasma (PRP). An aliquot of PRP was further subjected to centrifugation at 1,200×g for 20 minutes to obtain platelet-poor plasma (PPP). Numbers of the platelet were measured with an automatic platelet counter: Sysmex PL-100 (manufactured by Toa Iyodenshi Co.) and PRP was diluted with PPP so as to adjust a platelet concentration to be about 250,000 particles/µl. Platelet aggregation was measured by the following procedure with a 6 channel aggregometer: HEMA TRACER 1 (manufactured by NKK Co.)

After incubation of 240 µl of PRP at 37° C. for 2 minutes, 30 µl of the solvent of specimen as a control or the specimen in various concentrations was added to PRP. Further 2 minutes later, 30 µl of adenosine diphosphate (final concentration: 5 µM) was added to induce platelet aggregation. An inhibition percentage was obtained by comparing the maximum aggregation of the specimen drug group with that of control. A specimen drug concentration giving 50% inhibition ($IC_{50}$) was calculated from the inhibition percentage and the specimen drug concentration, and used as an index of antiplatelet activity. Results are illustrated in Table 3.

TABLE 3

Platelet aggregation inhibitory activity in human

| Compound | $IC_{50}$(nM) |
| --- | --- |
| Compound of Example 2 | 68 |
| Compound of Example 5 | 66 |
| Compound of Example 9 | 171 |
| Compound of Example 13 | 60 |
| Compound of Example 15 | 110 |
| Compound of Example 18 | 140 |
| Compound of Example 25 | 100 |
| Compound of Example 27 | 78 |
| Compound of Example 33 | 160 |
| Compound of Example 35 | 160 |
| Compound of Example 46 | 29 |
| Compound of Example 48 | 33 |
| Compound of Example 50 | 44 |
| Compound of Example 52 | 35 |

Pharmacological Test Example 3

Experiment for inhibition against platelet aggregation ability after oral administration The specimen drug was dissolved or suspended at a concentration of 18.5 µmol/ml in a physiological saline containing 0.5% of Tween 80. A Hartley strained male guinea pig (220–360 g) was starved overnight and the above obtained composition was introgastrically administered in an amount of 2 ml/kg body weight. A physiological saline containing 0.5% of Tween 80 was similarly administered as a control. After an hour, an abdominal operation was carried out under pentobarbital anesthesia, blood was collected from inferior vena cava, and 1 volume of a 3.8% aqueous sodium citrate solution was added as an anticoagulant for 9 volumes of the blood. The blood mixture was centrifuged at 800 r.p.m. for 20 minutes at room temperature to obtain PRP in the upper layer. The lower layer was further centrifuged at 3000 r.p.m. for 15 minutes to obtain PPP in upper layer. PRP was diluted with PPP so as to obtain a platelet concentration of 300,000 particles/µl in PRP. Platelet aggregation ability was measured according to the method for measuring in vitro platelet aggregation. Platelet aggregation ability was measured by the following procedures with a 6 channel aggregometer: HEMA TRACER 1 (manufactured by NKK Co.).

After incubation of PRP at 37° C. for 2 minutes, a physiological saline (30 µl) was added. Successively after 2 minutes, 30 µl of adenosine diphosphate (final concentration: 5 µM) was added to elicite platelet aggregation. An inhibiting ratio was obtained by comparing the maximum aggregation of the specimen drug group with that of control. Results are illustrated in Table 4.

TABLE 4

Inhibition against platelet aggregation in guinea pig (oral administration: 37 µmol/kg)

| Compound | Aggregation inhibiting rate (%) |
| --- | --- |
| Compound of Example 1 | >90 |
| Compound of Example 4 | >90 |
| Compound of Example 8 | >90 |
| Compound of Example 12 | >90 |
| Compound of Example 14 | >90 |
| Compound of Example 17 | >90 |
| Compound of Example 21 | >90 |
| Compound of Example 22 | >90 |

TABLE 4-continued

Inhibition against platelet aggregation in guinea pig
(oral administration: 37 μmol/kg)

| Compound | Aggregation inhibiting rate (%) |
|---|---|
| Compound of Example 24 | >90 |
| Compound of Example 26 | >90 |
| Compound of Example 29 | >90 |
| Compound of Example 31 | >90 |
| Compound of Example 34 | >90 |
| Compound of Example 38 | >90 |
| Compound of Example 40 | >90 |
| Compound of Example 45 | >90 |
| Compound of Example 47 | >90 |
| Compound of Example 49 | >90 |
| Compound of Example 51 | >90 |
| Compound of Reference Example 1 | 41 |
| Compound of Reference Example 3 | 39 |
| Compound of Reference example 5 | 10 |
| Compound of Reference Example 7 | 24 |
| Compound of Reference Example 9 | 3 |
| Compound of Reference Example 10 | 59 |

The compounds in Reference Example 1, 3, 5 and 7 have an unsubstituted amidino group. In Reference Example 9, the amidino group is substituted by an n-propyl group alone. In Reference Example 10, the amidino group is substituted by an alkoxycarbonyl group alone.

On the other hand, the compound of the invention which is represented by formula (1) had excellent efficacy on oral administration as compared with these compounds.

Formulation Examples

When the compound represented by formula (1) is used for a preventive or treatment of thrombosis and restenosis or reocclusion after percutaneous transluminal coronary angioplasty and percutaneous transluminal coronary recanalization, the compound can be used, for example, by the following formulations.

Formulation Example 1 (Tablet)

After thoroughly mixing 50 g of ethyl 7-[[4-(morpholinoiminomethyl)benzoyl]amino]-1,2,3,4-tetrahydronaphthalene-2-acetate hydrochloride, 38 g of lactose, 35 g of corn starch and 20 g of crystalline cellulose, the mixture was subjected to scouring granulation with an aqueous solution containing 5 g of hydroxypropyl cellulose and dried at 50° C. for 4 hours. To the granule obtained, 2 g of magnesium stearate was added and thoroughly mixed. The mixture thus obtained was subjected to tablet making with a tabletting machine to form tablets having a weight of 150 mg/tablet.

Formulation Example 2 (Tablet)

After thoroughly mixing 50 g of ethyl (-)-6-[[4-(morpholinoiminomethyl)benzoyl]amino]chroman-3-acetate hydrochloride, 38 g of lactose, 35 g of corn starch and 20 g of crystalline cellulose, the mixture was subjected to scouring granulation with an aqueous solution containing 5 g of hydroxypropyl cellulose and dried at 50° C. for 4 hours. To the granule obtained, 2 g of magnesium stearate was added and thoroughly mixed. The mixture thus obtained was subjected to tablet making with a tabletting machine to form tablets having a weight of 150 mg/tablet.

Formulation Example 3 (Capsule)

After thoroughly mixing 100 g of ethyl 7-[[4-(morpholinoiminomethyl)benzoyl]amino]-1,2,3,4-tetrahydronaphthalene-2-acetate hydrochloride, 70 g of lactose, 70 g of corn starch, 40 g of crystalline cellulose and 6 g of magnesium stearate, the mixture obtained was packed into a hard gelatin capsule with a plugger to form capsules having a content of 300 mg.

Formulation Example 4 (Granules)

After thoroughly mixing 100 g of ethyl 7-[[4-(thiomorpholinoiminomethyl)benzoyl]amino]-1,2,3,4-tetrahydronaphthalene-2-acetate hydrochloride, 150 g of lactose, 140 g of corn starch and 80 g of crystalline cellulose, the mixture was subjected to scouring granulation with a solution containing 20 g of hydroxypropyl cellulose in 400 ml of water and dried at 50° C. for 4 hours. The granulated mass was graded by passing through a 12 mesh screen and thoroughly mixed with 8 g of magnesium stearate to obtain granules.

Formulation Example 5 (Injection)

Ethyl 7-[[4-(morpholinoiminomethyl)benzoyl]amino]-1,2,3,4-tetrahydroisoquinoline-2-acetate dihydrochloride (0.5 g) was dissolved in physiological saline (10 ml), filtered through a membrane filter, and subjected again to sterilyzing filtration. The filtrate was aseptically charged into a vial, packed with nitrogen gas and sealed to obtain an intravenous injection.

What is claimed is:

1. A substituted amidine derivative represented by formula (1):

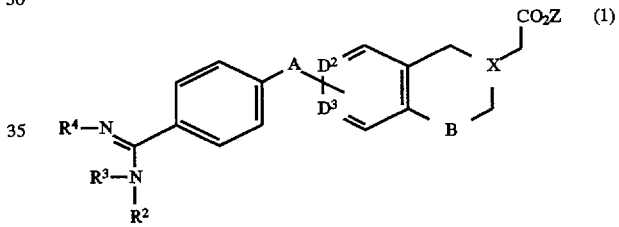

wherein A is —CON($R^1$)— or —N($R^1$)CO— and is bonded to $D^2$ or $D^3$, wherein $R^1$ is a hydrogen atom or an alkyl group having 1–4 carbon atoms, and $D^2$ and $D^3$ is a carbon atom; B is —O— and X is

Z is a hydrogen atom, an unsubstituted or substituted alkyl group; $R^2$, $R^3$ and $R^4$ are a hydrogen atom, alkyl group having 1–4 carbon atoms, propargyl group, $R^5$—O(CO)— or —$(CH_2)_m$-Het, wherein $R^5$ is an alkyl group having 1–4 carbon atoms or 2-methyoxyethyl group, m is an integer of 1 or 2, Het is a pyridyl, furyl or thienyl group, or $R^2$ and $R^3$ are bonded to form —$(CH_2)_n$—W—$(CH_2)_p$—, wherein n and p are an integer of 2 or 3, a certain position on the methylene chain is unsubstituted or substituted with an alkyl group having 1–4 carbon atoms or an alkoxy group having 1–4 carbon atoms, W is a direct bond, —$CH_2$—, —O—, —N($R^6$)— or —$S(O)_q$, wherein $R^6$ is an alkyl group having 1–4 carbon atoms, phenyl group or pyridyl group and q is 0 or an integer of 1 or 2; with the proviso that at least one group of $R^2$, $R^3$ and $R^4$ is selected from the group consisting of propargyl group and —$(CH_2)_m$-Het, or $R^2$ and $R^3$ are bonded to form —$(CH_2)_n$—W—$(CH_2)_p$—; or a pharmaceutically acceptable salt thereof.

2. The substituted amidine derivative according to claim 1 wherein A is bonded to $D^2$.

3. The substituted amidine derivative according to claim 2 wherein $R^2$ and $R^3$ are bonded to form —$(CH_2)_n$—W—$(CH_2)_p$— and W is selected from a direct bond, —$CH_2$—, —O—, —S— or —$N(R^6)$—.

4. The substituted amidine derivative according to claim 3 wherein A is —NHCO— or —CONH—.

5. A pharmaceutical composition of matter comprising a compound according to claim 2 in an amount effective for inhibiting platelet aggregation and a pharmaceutically acceptable diluent and/or carrier therefor.

6. A pharmaceutical composition of matter comprising a compound according to claim 1 in an amount effective for inhibiting platelet aggregation and a pharmaceutically acceptable diluent and/or carrier therefor.

7. A pharmaceutical composition of matter comprising a compound according to claim 3 in an amount effective for inhibiting platelet aggregation and a pharmaceutically acceptable diluent and/or carrier therefor.

8. A pharmaceutical composition of matter comprising a compound according to claim 4 in an amount effective for inhibiting platelet aggregation and a pharmaceutically acceptable diluent and/or carrier therefor.

9. A method for preventing or treating thrombosis comprising administering an effective dose of the compound according to claim 1.

10. A method for preventing or treating thrombosis comprising administering an effective dose of the compound according to claim 2.

11. A method for preventing or treating thrombosis comprising administering an effective dose of the compound according to claim 3.

12. A method for preventing or treating thrombosis comprising administering an effective dose of the compound according to claim 4.

13. A method for preventing or treating restenosis after percutaneous transluminal coronary angioplasty or percutaneous transluminal coronary recanalization, comprising administering an effective dose of the compound according to claim 1.

14. A method for preventing or treating restenosis after percutaneous transluminal coronary angioplasty or percutaneous transluminal coronary recanalization, comprising administering an effective dose of the compound according to claim 2.

15. A method for preventing or treating restenosis after percutaneous transluminal coronary angioplasty or percutaneous transluminal coronary recanalization, comprising administering an effective dose of the compound according to claim 3.

16. A method for preventing or treating restenosis after percutaneous transluminal coronary angioplasty or percutaneous transluminal coronary recanalization, comprising administering an effective dose of the compound according to claim 4.

17. A method for preventing or treating reocclusion after percutaneous transluminal coronary angioplasty or percutaneous transluminal coronary recanalization, comprising administering an effective dose of the compound according to claim 1.

18. A method for preventing or treating reocclusion after percutaneous transluminal coronary angioplasty or percutaneous transluminal coronary recanalization, comprising administering an effective dose of the compound according to claim 2.

19. A method for preventing or treating reocclusion after percutaneous transluminal coronary angioplasty or percutaneous transluminal coronary recanalization, comprising administering an effective dose of the compound according to claim 3.

20. A method for preventing or treating reocclusion after percutaneous transluminal coronary angioplasty or percutaneous transluminal coronary recanalization, comprising administering an effective dose of the compound according to claim 4.

* * * * *

UNITED STATES PATENT AND TRADEMARK OFFICE
CERTIFICATE OF CORRECTION

PATENT NO. : 5,719,145

DATED: : February 17, 1998

INVENTOR(S) : Yamashita et al

It is certified that error appears in the above-identified patent and that said Letters Patent is hereby corrected as shown below:

1) As set forth in the Claim for Convention Priority filed on November 6, 1997, please add the following priority data:

7-223094    August 31, 1995    Japan

2) As set forth in the Information Disclosure Statement filed on October 1, 1996, please amend the first publication listed under "Other Publications" as follows:

Cook et al, "Platelet Glycoprotein IIB/IIIa Antagonists", *Drugs of the Future*, 19(2), pp. 135-159 (1994).

Signed and Sealed this

Twenty-ninth Day of December, 1998

Attest:

BRUCE LEHMAN

*Attesting Officer*     *Commissioner of Patents and Trademarks*